(12) United States Patent
Kuraguntla et al.

(10) Patent No.: US 9,924,905 B2
(45) Date of Patent: *Mar. 27, 2018

(54) SENSOR POSITION ON A PROSTHESIS FOR DETECTION OF A STENOSIS

(71) Applicant: GraftWorx, Inc., Menlo Park, CA (US)

(72) Inventors: David John Kuraguntla, Bel Air, MD (US); Samit Kumar Gupta, Bel Air, MD (US); Robert Lawrence Rushenberg, Omaha, NE (US)

(73) Assignee: Graftworx, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/064,318

(22) Filed: Mar. 8, 2016

(65) Prior Publication Data

US 2016/0262700 A1 Sep. 15, 2016

Related U.S. Application Data

(60) Provisional application No. 62/130,465, filed on Mar. 9, 2015.

(51) Int. Cl.
*A61F 2/07* (2013.01)
*A61B 5/103* (2006.01)
(Continued)

(52) U.S. Cl.
CPC .......... *A61B 5/6862* (2013.01); *A61B 5/0031* (2013.01); *A61B 5/02007* (2013.01); *A61B 5/076* (2013.01); *A61B 5/4848* (2013.01); *A61B 5/6876* (2013.01); *A61F 2/06* (2013.01); *A61B 5/026* (2013.01); *A61B 5/1468* (2013.01); *A61B 5/14507* (2013.01); *A61B 5/407* (2013.01); *A61B 5/4064* (2013.01); *A61B 5/4851* (2013.01);
(Continued)

(58) Field of Classification Search
CPC ..... A61F 2/82; A61F 2/06; A61F 2/07; A61B 5/6862
USPC .................................................. 623/1.1–1.48
See application file for complete search history.

(56) References Cited

U.S. PATENT DOCUMENTS 4,307,618 A 12/1981 James et al.
4,575,371 A 3/1986 Nordqvist et al.
(Continued)

FOREIGN PATENT DOCUMENTS

JP 4011631 B2 11/2007
JP 2009542421 A 12/2009
(Continued)

OTHER PUBLICATIONS

International Search Report and Written Opinion dated May 26, 2016 for International PCT Patent Application No. PCT/US16/21441.

(Continued)

*Primary Examiner* — Suzette J Gherbi
(74) *Attorney, Agent, or Firm* — Wilson Sonsini Goodrich & Rosati

(57) ABSTRACT

A prosthesis for monitoring a stenosis in the prosthesis comprises a tubular prosthesis having a proximal portion, a distal portion, and a lumen extending therebetween. A sensor is coupled to the tubular prosthesis and disposed at an effective predetermined location on the tubular prosthesis so that the sensor may sense a presence of the stenosis in the lumen.

27 Claims, 32 Drawing Sheets

(51) Int. Cl.
*A61B 5/00* (2006.01)
*A61F 2/06* (2013.01)
*A61B 5/02* (2006.01)
*A61B 5/07* (2006.01)
A61F 2/82 (2013.01)
A61B 5/026 (2006.01)
A61B 5/145 (2006.01)
A61B 5/1468 (2006.01)

(52) U.S. Cl.
CPC ............... *A61B 2560/0219* (2013.01); *A61B 2560/0462* (2013.01); *A61B 2562/0204* (2013.01); *A61F 2/07* (2013.01); *A61F 2/82* (2013.01); *A61F 2250/0096* (2013.01)

(56) References Cited

U.S. PATENT DOCUMENTS

| | | | |
|---|---|---|---|
| 4,600,855 A | 7/1986 | Strachan | |
| 4,920,794 A | 5/1990 | Ingman | |
| 5,241,964 A | 9/1993 | McQuilkin | |
| 5,409,009 A | 4/1995 | Olson | |
| 5,411,551 A | 5/1995 | Winston et al. | |
| 5,522,391 A | 6/1996 | Beaudin et al. | |
| 5,522,394 A | 6/1996 | Zurbruegg | |
| 5,598,841 A | 2/1997 | Taniji et al. | |
| 5,598,847 A | 2/1997 | Renger | |
| 5,681,274 A | 10/1997 | Perkins et al. | |
| 5,760,530 A | 6/1998 | Kolesar | |
| 5,785,657 A | 7/1998 | Breyer et al. | |
| 5,807,258 A | 9/1998 | Cimochowski et al. | |
| 5,967,986 A | 10/1999 | Cimochowski et al. | |
| 5,995,860 A | 11/1999 | Sun et al. | |
| 6,004,348 A | 12/1999 | Banas et al. | |
| 6,015,387 A | 1/2000 | Schwartz et al. | |
| 6,049,727 A | 4/2000 | Crothall | |
| 6,053,873 A | 4/2000 | Govari et al. | |
| 6,173,197 B1 | 1/2001 | Boggett et al. | |
| 6,193,669 B1 | 2/2001 | Degany et al. | |
| 6,354,999 B1 | 3/2002 | Degany et al. | |
| 6,416,474 B1 | 7/2002 | Penner et al. | |
| 6,458,086 B1 | 10/2002 | Franco et al. | |
| 6,486,588 B2 | 11/2002 | Doron et al. | |
| 6,682,480 B1 | 1/2004 | Habib et al. | |
| 6,764,519 B2 | 7/2004 | Whitmore | |
| 6,840,956 B1 | 1/2005 | Wolinsky et al. | |
| 7,025,778 B2 | 4/2006 | Hayashi et al. | |
| 7,060,038 B2 | 6/2006 | Letort et al. | |
| 7,261,733 B1 | 8/2007 | Brown et al. | |
| 7,267,651 B2 | 9/2007 | Nelson | |
| 7,399,313 B2 | 7/2008 | Brown et al. | |
| 7,488,345 B2 | 2/2009 | Brown et al. | |
| 7,572,228 B2 | 8/2009 | Wolinsky et al. | |
| 7,650,185 B2 | 1/2010 | Maile et al. | |
| 7,686,842 B2 | 3/2010 | Pavcnik et al. | |
| 7,747,302 B2 | 6/2010 | Milledge et al. | |
| 7,747,329 B2 | 6/2010 | Litvak et al. | |
| 7,785,912 B2 | 8/2010 | Zhan et al. | |
| 7,813,808 B1 | 10/2010 | Doron et al. | |
| 7,918,800 B1 | 4/2011 | Brown et al. | |
| 7,922,667 B2 | 4/2011 | Gianchandani et al. | |
| 7,948,148 B2 | 5/2011 | Porat et al. | |
| 7,949,394 B2 | 5/2011 | Salo et al. | |
| 7,963,920 B2 | 6/2011 | Vilkomerson et al. | |
| 8,016,875 B2 | 9/2011 | Philipp et al. | |
| 8,034,096 B2 | 10/2011 | Hunt | |
| 8,114,350 B1 | 2/2012 | Silver et al. | |
| 8,202,311 B2 | 6/2012 | Demetriades et al. | |
| 8,211,165 B1 | 7/2012 | McIntosh et al. | |
| 8,211,166 B2 | 7/2012 | Chuter et al. | |
| 8,211,168 B2 | 7/2012 | Purdy et al. | |
| 8,216,434 B2 | 7/2012 | Hsiai et al. | |
| 8,308,794 B2 | 11/2012 | Martinson et al. | |
| 8,551,156 B2 | 10/2013 | Wack et al. | |
| 8,579,958 B2 | 11/2013 | Kusleika | |
| 8,597,343 B2 | 12/2013 | Bliss et al. | |
| 8,628,491 B2 | 1/2014 | Kahn et al. | |
| 9,662,021 B2 | 5/2017 | Chow et al. | |
| 2001/0041932 A1 | 11/2001 | Scholz et al. | |
| 2001/0049554 A1 | 12/2001 | Ruiz et al. | |
| 2002/0183628 A1 | 12/2002 | Reich et al. | |
| 2003/0229388 A1 | 12/2003 | Hayashi et al. | |
| 2004/0082867 A1 | 4/2004 | Esch et al. | |
| 2004/0082868 A1 | 4/2004 | Campbell et al. | |
| 2004/0249293 A1 | 12/2004 | Sandler et al. | |
| 2005/0165317 A1 | 7/2005 | Turner et al. | |
| 2005/0210988 A1 | 9/2005 | Amano et al. | |
| 2005/0277839 A1 | 12/2005 | Alderman et al. | |
| 2006/0020239 A1 | 1/2006 | Geiger et al. | |
| 2006/0074479 A1 | 4/2006 | Bailey et al. | |
| 2006/0079782 A1 | 4/2006 | Beach et al. | |
| 2006/0129050 A1 | 6/2006 | Martinson et al. | |
| 2008/0033527 A1 | 2/2008 | Nunez et al. | |
| 2008/0278336 A1 | 11/2008 | Ortega et al. | |
| 2009/0295383 A1 | 12/2009 | Gianchandani et al. | |
| 2010/0198329 A1* | 8/2010 | Kassab | A61B 17/00491 623/1.13 |
| 2011/0054333 A1 | 3/2011 | Hoffer | |
| 2011/0301882 A1 | 12/2011 | Andersen | |
| 2012/0053666 A1* | 3/2012 | Ferren | A61B 1/00156 607/119 |
| 2012/0058012 A1 | 3/2012 | Silver et al. | |
| 2012/0271200 A1* | 10/2012 | Martinson | A61B 5/07 600/587 |
| 2013/0178750 A1* | 7/2013 | Sheehan | A61F 2/2403 600/486 |
| 2013/0331919 A1 | 12/2013 | Zhang et al. | |
| 2014/0214149 A1* | 7/2014 | Kuraguntla | A61F 2/852 623/1.15 |
| 2014/0228943 A1* | 8/2014 | Stigall | A61F 2/2436 623/2.11 |
| 2014/0316289 A1 | 10/2014 | Kassab | |
| 2014/0336497 A1* | 11/2014 | Gertner | A61B 5/055 600/411 |
| 2015/0018643 A1 | 1/2015 | Cole et al. | |
| 2015/0025394 A1 | 1/2015 | Hong et al. | |
| 2016/0000568 A1* | 1/2016 | Kassab | A61F 2/07 604/9 |
| 2016/0038087 A1* | 2/2016 | Hunter | A61B 5/6862 600/301 |
| 2016/0193031 A1* | 7/2016 | Kassab | A61B 17/12113 623/1.13 |
| 2016/0331312 A1 | 11/2016 | Kuraguntla et al. | |
| 2016/0331313 A1 | 11/2016 | Karaguntla et al. | |

FOREIGN PATENT DOCUMENTS

| | | |
|---|---|---|
| WO | WO-9942039 A1 | 8/1999 |
| WO | WO-2002000118 A2 | 1/2002 |
| WO | WO-2006086435 A2 | 8/2006 |
| WO | WO-2008006003 A2 | 1/2008 |
| WO | WO-2014100795 A1 | 6/2014 |
| WO | WO-2016110804 A1 | 7/2016 |

OTHER PUBLICATIONS

Kistler, et al. The bruit of carotid stenosis versus radiated basal heart murmurs. Differentiation by phonoangiography. Circulation. May 1978;57(5):975-81.
Knox, et al. Quantitative carotid phonoangiography. Stroke. Nov.-Dec. 1981;12(6):798-803.
Dario, et al. Monitoring of prosthetic vascular grafts using piezoelectric polymer sensors. Trans Am Soc Artif Intern Organs. 1983;29:318-22.
Gupta, et al. Use of a piezoelectric film sensor for monitoring vascular grafts. Am J Surg. Aug. 1990;160(2):182-5; discussion 185-6.
International search report and written opinion dated Apr. 14, 2014 for PCT/US2014/013068.
International search report and written opinion dated May 14, 2015 for PCT/US2015/015502.

(56) References Cited

OTHER PUBLICATIONS

International Search Report and Written Opinion dated May 19, 2016 for International PCT Patent Application No. PCT/US2016/021026.

Neville, et al. An expanded series of distal bypass using the distal vein patch technique to improve prosthetic graft performance in critical limb ischemia. Eur J Vasc Endovasc Surg. Aug. 2012;44(2):177-82. doi: 10.1016/j.ejvs.2012.04.014. Epub May 15, 2012.

Notice of Allowance dated Jun. 8, 2016 for U.S. Appl. No. 14/163,991.

Office action dated Jan. 5, 2016 for U.S. Appl. No. 14/163,991.

Tsagakis, et al. Overall Essen's experience with the E-vita open hybrid stent graft system and evolution of the surgical technique. Ann Cardiothorac Surg. Sep. 2013;2(5):612-20. doi: 10.3978/j.issn.2225-319X.2013.09.17.

International Search Report and Written Opinion dated Nov. 17, 2017 for International PCT Patent Application No. PCT/US2017/051213.

Office Action dated Sep. 22, 2017 for U.S. Appl. No. 14/619,948.

\* cited by examiner

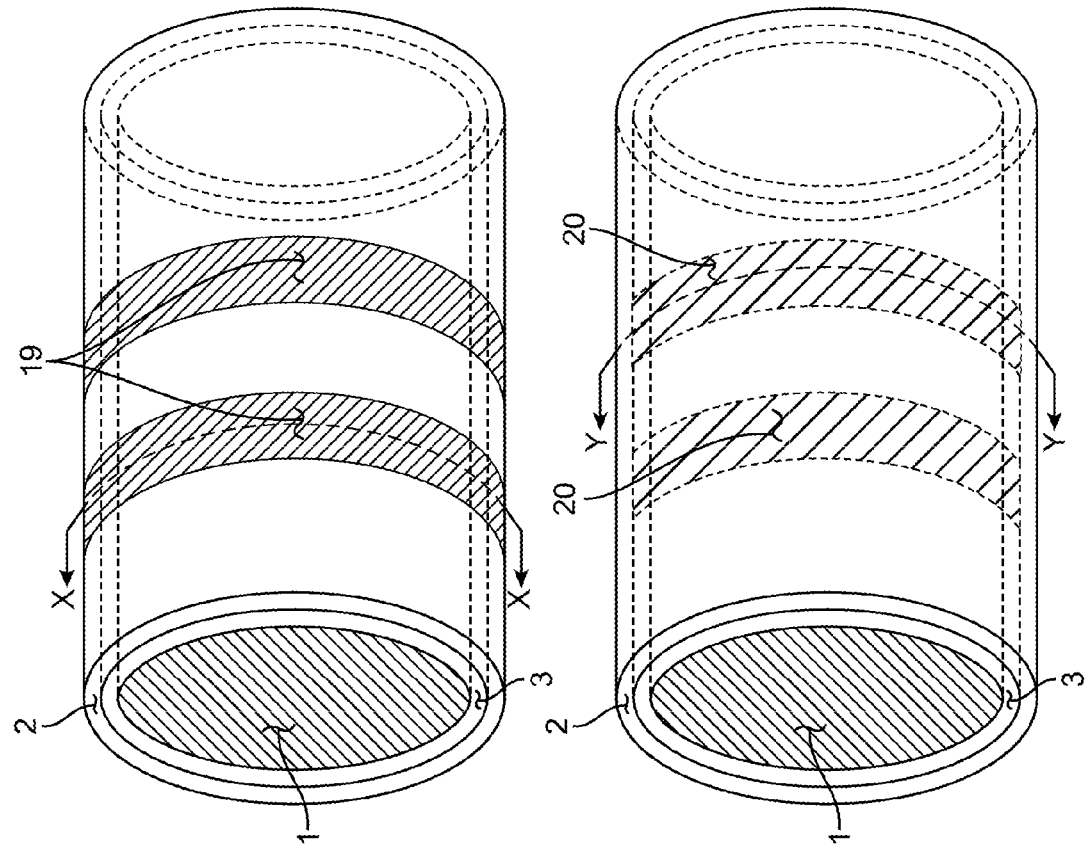
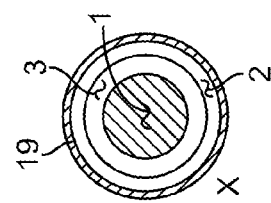
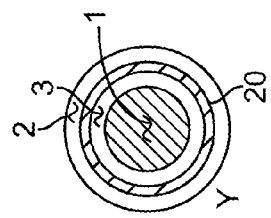
FIG. 8A  FIG. 8A1  FIG. 8B  FIG. 8B1

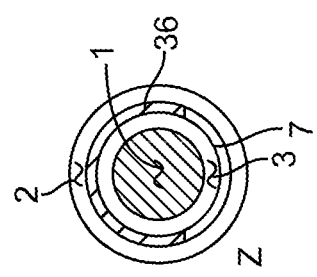
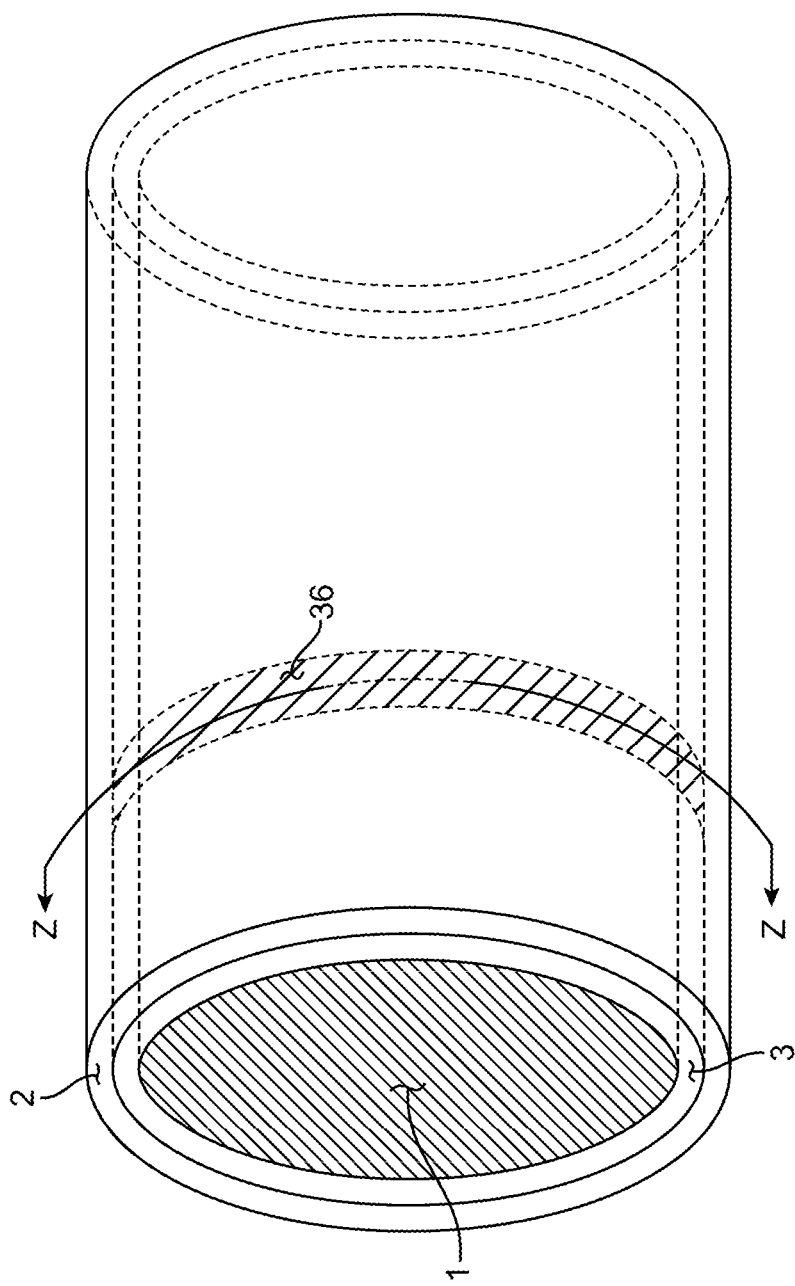
FIG. 15A
FIG. 15

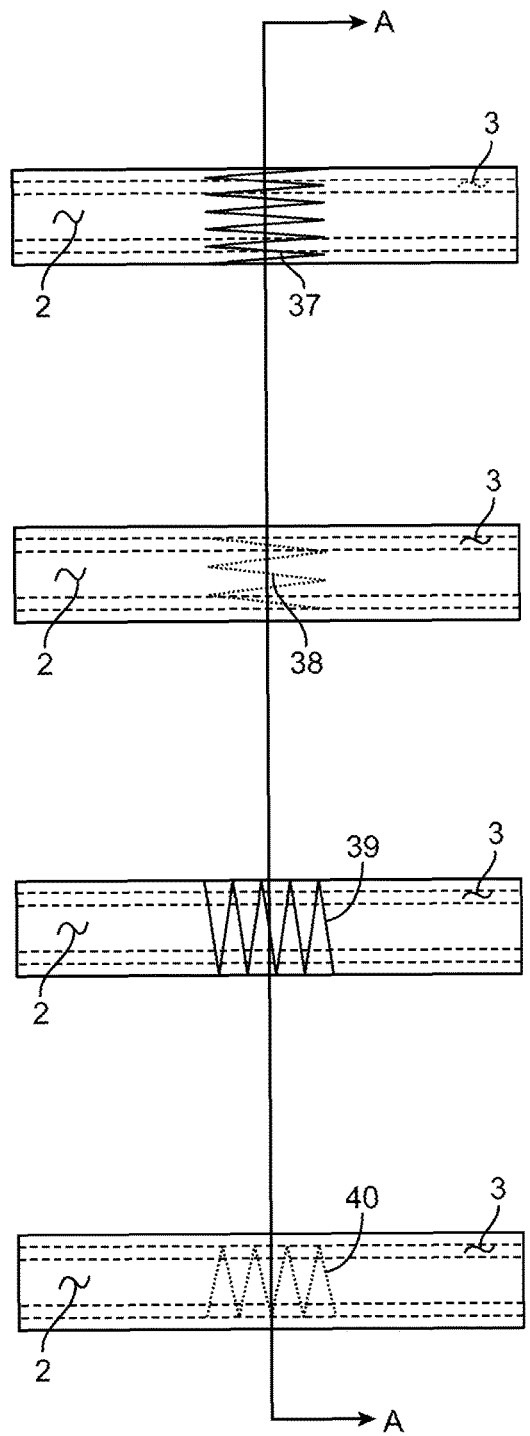
FIG. 16A
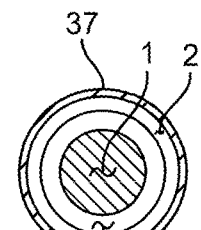
FIG. 16A1
FIG. 16B
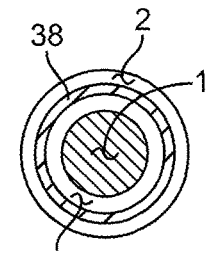
FIG. 16B1
FIG. 16C
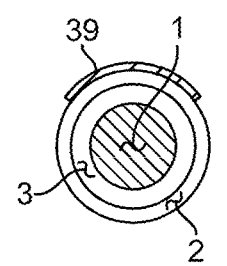
FIG. 16C1
FIG. 16D
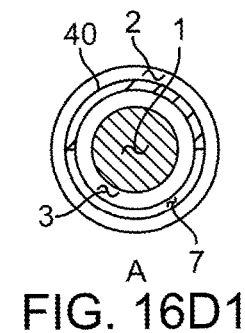
FIG. 16D1

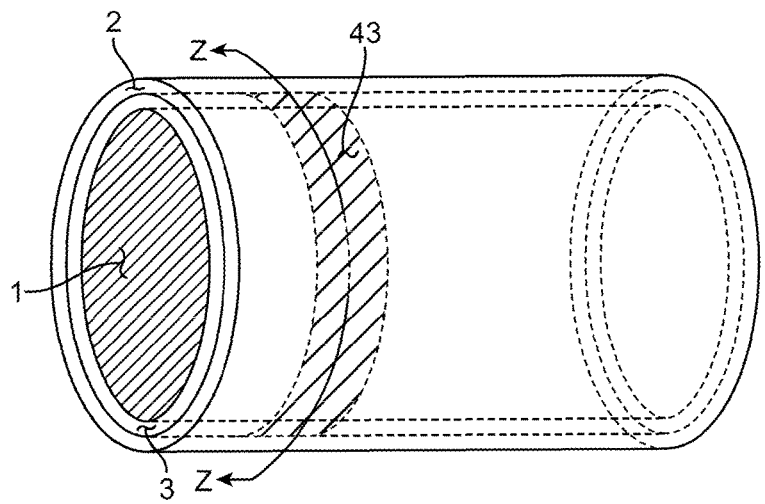
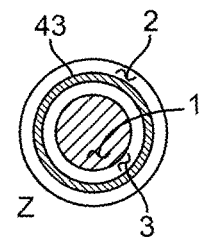
FIG. 18A
FIG. 18B
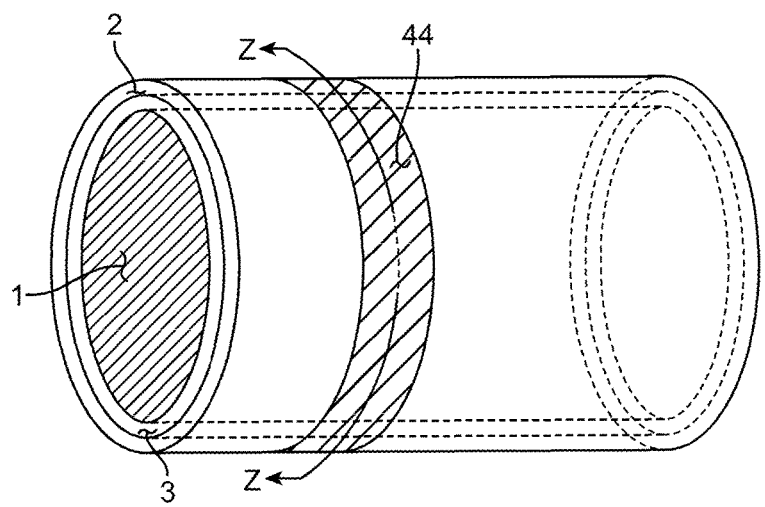
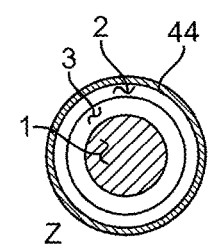
FIG. 18C
FIG. 18D

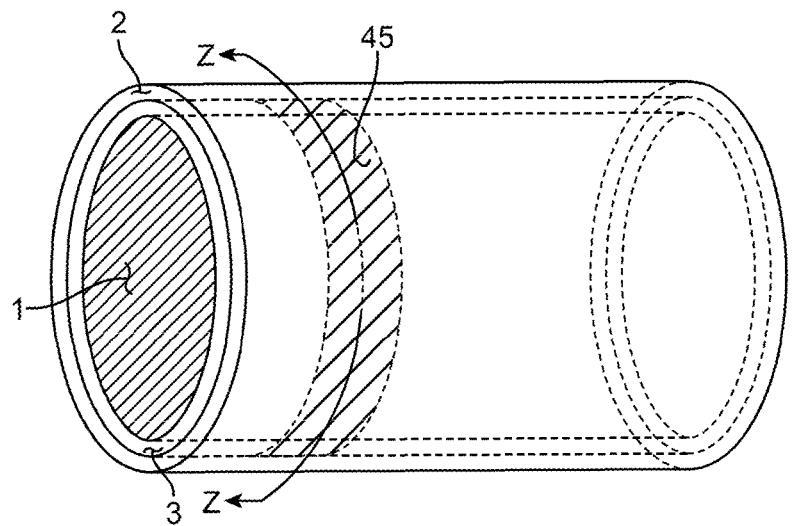 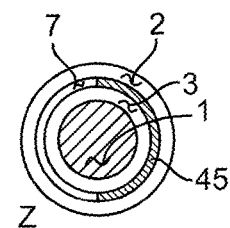
FIG. 19A
FIG. 19B
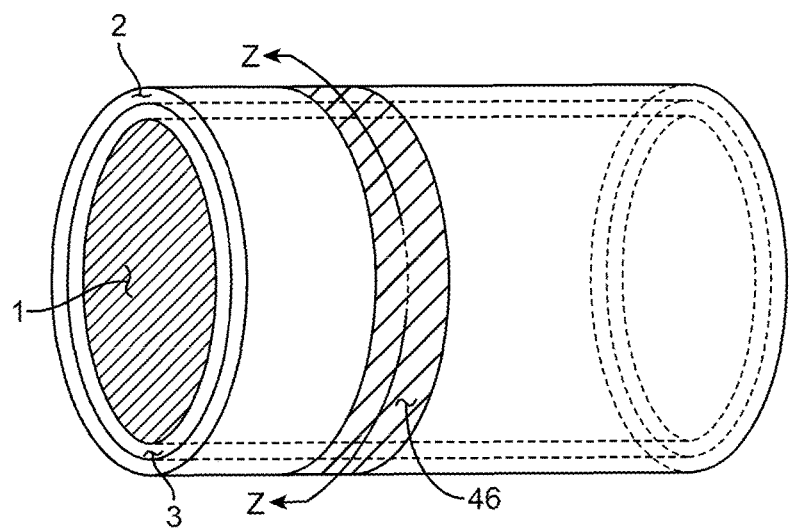 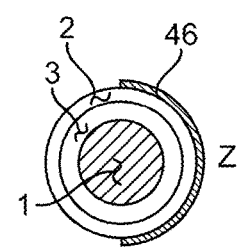
FIG. 19C
FIG. 19D

SENSOR POSITION ON A PROSTHESIS FOR DETECTION OF A STENOSIS

CROSS-REFERENCE TO RELATED APPLICATIONS

The present application is a non-provisional of, and claims the benefit of U.S. Provisional Patent Application No. 62/130,465 filed Mar. 9, 2015; the entire contents of which are incorporated herein by reference.

The present application is related to U.S. patent application Ser. No. 14/163,991 filed Jan. 24, 2014; the entire contents of which are incorporated herein by reference.

BACKGROUND OF THE INVENTION

1. Field of the Invention

The present application generally relates to medical devices, systems and methods, and more particularly relates to medical devices, systems, and methods for detection and monitoring of flow and/or a stenosis in a prosthesis.

Peripheral arterial disease (PAD) refers to the obstruction of arteries other than those supplying the heart and within the brain. A common denominator among pathologic processes is the impairment of circulation and resultant ischemia to the end organ involved. Without being bound by any particular theory, the following pathologies and their mechanisms of action are believed to be relevant. Atherosclerosis is the most common pathology associated with PAD. It is a hardening of an artery specifically caused by an atheromatous plaque. Hyperlipidemia, hypercholesterolemia, hypertension, diabetes mellitus, and exposure to infectious agents or toxins such as from cigarette smoking are all important and independent risk factors for atherosclerosis. The common mechanism is thought to be endothelial cell injury, smooth muscle cell proliferation, inflammatory reactivity, and plaque deposition.

Several components are found in atherosclerotic plaque—lipids, smooth muscle cells, connective tissue and inflammatory cells, often macrophages. Lipid accumulation is central to the process and distinguishes atheromas from other arteriopathies. In advanced plaques, calcification is seen and erosive areas or ulcerations can occur, exposing the contents of the plaque to circulating prothrombotic cells. In the event of plaque rupture the contents of the lipid core are exposed to circulating humoral factors, the body, perceiving the ulceration as an injury, may lay down platelets and initiate clot formation.

Ischemia can result from a number of possible plaque behaviors, such as encroachment on the lumen (stenosis or narrowing) with hypoperfusion, stagnation, and thrombosis; rupture of the fibrous cap inducing thrombus formation in the lumen, with outright occlusion; and embolization of thrombotic debris into the downstream circulation. There is an interestingly predictable pattern of distribution of atheromatous plaques throughout the arterial tree that is likely a result of consistent hemodynamic stresses associated with human anatomic design. Atheromatous plaques tend to occur at bifurcations or at bends associated with repetitive external stresses. Areas of increased shear stress due to disturbances in flow or turbulence, with lateralizing vectors and eddy formation, are prone to atheromatous degeneration.

Due to the insidious nature of PAD and renal failure, 1.4 million arterial bypass procedures are performed in the United States to alleviate the consequences of inadequate blood flow. Of these arterial bypass procedures, 450,000 utilize a synthetic vascular graft. The number of total bypass procedures is increasing along with an aging population. The percentage of bypass procedures which utilize a synthetic graft is also increasing due to the rising incidence of diabetes and obesity. After successful surgical placement, bypass grafts are at a high risk for failure from a number of factors. Factors predisposing to graft failure include the progression of vascular disease and promotion of clotting factors.

Synthetic graft placement can cause fibrosis due to intimal hyperplasia and is a major cause of bypass graft failure. In an end-to-side configuration of synthetic graft placement, abnormal shear stress conditions are thought to occur, contributing to the development of intimal hyperplasia. Intimal hyperplasia is a physiologic healing response to injury to the blood vessel wall. When the vascular endothelium is injured, endothelial cells release inflammatory mediators that trigger platelet aggregation, fibrin deposition and recruitment of leukocytes to the area. These cells express growth factors that promote smooth muscle cell migration from the media to the tunica intima. The smooth muscle cells proliferate in the intima and deposit extracellular matrix, in a process analogous to scar formation.

The presence of prosthetic material in the vessel seems to accelerate the development of intimal hyperplasia. Restenosis occurring 3 to 12 months after intervention is typically due to intimal hyperplasia. Stenosis from intimal hyperplasia is often difficult to treat. Unlike soft atheromatous plaques, these stenoses are firm and require prolonged high inflation pressures to dilate with a balloon. These stenoses often recur; repeated dilatation causes repeated intimal injury and perpetuates the intimal healing response. While there have been significant advances in the field, such as, drug-eluting stents, drug coated angioplasty balloons, systemic low-dose low molecular weight heparin, and systemic low-dose warfarin; the deleterious effects of intimal hyperplasia have not been resolved.

Graft failure leads to disastrous consequences for the patient, such as tissue ischemia and limb loss. Not infrequently, amputations in the vascular patients are prone to breakdown and then need for revision is common, thereby prolonging the patient's time in the hospital, lengthening the recovery process decreasing the chances of functional recovery, and contributing to a high rate of depression. In addition to the financial cost of treatment and lost wages, there is a significant cost to the patient in terms of decreased mobility, potential loss of employment and decreased quality of life.

Currently, vascular grafts are monitored after surgical placement by either angiography or duplex ultrasonography. These tests are typically repeated periodically, e.g., at six month intervals, since restenosis precipitating graft failure is prevalent. Grayscale (B-mode) ultrasound is employed to visualize the architecture of the graft. Color Doppler ultrasound visualizes the blood flow velocity (cm/s) or flow rate within the lumen. Severe calcification of the distal vessels or the vascular graft can impede imaging of flow. Given the various physiologic factors and outside influences (i.e. operator dependence) affecting the outcome of these tests, it is difficult to quantitatively ascertain the results of the procedure with any degree of accuracy or precision. Due to the burdensome nature of this technique, the medical practitioner will only get two or three opportunities to characterize the patency of the vascular graft during the first year. It would therefore be advantageous to provide improved methods and devices for detecting and monitoring blood flow through the synthetic graft or a stenosis in the graft, immediately following surgical implantation and thereafter, either periodically or on a continuous basis. At least some of these objectives will be satisfied by the exemplary methods and devices described below.

2. Description of the Background Art

References which may be related to measuring flow through a prosthesis include U.S. Pat. Nos. 8,216,434; 8,211,165; 8,211,166; 8,211,168; 6,486,588; 7,785,912; 5,807,258; 7,650,185; 7,963,920; 8,016,875; 5,967,986; 7,813,808; 6,458,086; 5,409,009; 5,598,841; 5,995,860; 6,049,727; 6,173,197; 7,267,651; 6,682,480; 6,053,873; 5,522,394; 7,488,345; 7,025,778; 7,922,667; 5,785,657; 7,949,394; 7,948,148; 4,600,855; 5,411,551; 5,598,847; 7,918,800; 5,760,530; 4,920,794; 8,308,794; 7,747,329; 7,572,228; 7,399,313; 7,261,733; 7,060,038; 6,840,956; 6,416,474; 6,015,387; 5,967,986; 5,807,258; and US Patent Publication Nos. 2005/0210988; 2004/0082867; 2012/0058012; 2011/0054333; 2008/0033527; 2005/0277839; 2002/0183628 and 2002/0183628.

SUMMARY OF THE INVENTION

The present invention generally relates to medical systems, devices and methods, and more particularly relates to detection and monitoring of a stenosis in prosthesis.

In a first aspect, a prosthesis for monitoring a stenosis therein, comprises a tubular prosthesis having a proximal portion, a distal portion, and a lumen extending therebetween, and the prosthesis also comprises a sensor coupled to the tubular prosthesis and disposed at an effective predetermined location on the tubular prosthesis, wherein the sensor is configured to sense a presence of the stenosis in the lumen.

The sensor may comprise an acoustic sensor. The sensor may be disposed in the proximal portion or the distal portion of the prosthesis. The stenosis may be disposed distal of the sensor, and the sensor may be configured to sense the presence of the stenosis in the lumen. The sensor may be disposed no more than 0 cm to about 3 cm away from the stenosis. The tubular prosthesis may be a graft and the proximal portion of the prosthesis may be adapted to be coupled to a native fluid conduit at a proximal anastomotic site, and the distal portion of the prosthesis may be adapted to be coupled to the native fluid conduit at a distal anastomotic site, and the sensor may be disposed no more than 0 cm to about 3 cm away from the distal anastomotic site. The tubular prosthesis may be a graft and the proximal portion of the prosthesis may be adapted to be coupled to a native fluid conduit at a proximal anastomotic site, and the distal portion of the prosthesis may be adapted to be coupled to the native fluid conduit at a distal anastomotic site, and wherein the sensor is disposed no more than 0 cm to about 15 cm away from the proximal anastomotic site.

In any of the embodiments, the native fluid conduit may comprise a blood vessel. The tubular prosthesis may be a stent or a stent-graft. Only a single sensor may be coupled to the prosthesis. The sensor may be disposed circumferentially around the tubular prosthesis. The sensor may form a loop around the tubular prosthesis.

The prosthesis may comprise a plurality of sensors disposed on the tubular prosthesis and spaced a predetermined distance apart from one another, thereby allowing the plurality of sensors to detect the stenosis, wherein the stenosis forms along any portion of the tubular prosthesis. The prosthesis may be a stent, and the prosthesis may further comprise a plurality of sensors disposed on the stent and spaced a predetermined distance apart from one another, thereby allowing the plurality of sensors to detect the stenosis, wherein the stenosis forms along any portion of the stent. The predetermined distance may be about 18 cm apart.

In another aspect, a method for monitoring a stenosis in a prosthesis comprises providing a tubular prosthesis having a sensor coupled thereto, implanting the tubular prosthesis in a native fluid conduit, sensing a stenosis in a lumen of the tubular prosthesis with the sensor; and reporting out data from the sensor regarding a condition the stenosis.

The sensor may be an acoustic sensor, and sensing the stenosis may comprise acoustically sensing the stenosis with the acoustic sensor. Sensing may comprise sensing the stenosis with the sensor disposed in a proximal portion or a distal portion of the tubular prosthesis. Sensing may comprise sensing the stenosis with the sensor disposed no more than 0 cm to about 3 cm away from the stenosis.

The tubular prosthesis may be a graft, and implanting the tubular prosthesis may comprise forming a distal anastomosis between the native fluid conduit and a distal portion of the graft, and wherein the sensing comprises sensing the stenosis with the sensor disposed no more than 0 cm to about 3 cm away from the distal anastomosis. Also, the tubular prosthesis may be a graft and implanting the tubular prosthesis may comprise forming a proximal anastomosis between the native fluid conduit and a proximal portion of the graft, and the sensing may comprise sensing the stenosis with the sensor disposed no more than 0 cm to about 15 cm away from the proximal anastomosis. Sensing may comprise sensing the stenosis with the sensor when the stenosis is distal of the sensor.

The native fluid conduit may comprise a blood vessel. Sensing may comprise sensing the stenosis with only a single sensor coupled to the prosthesis. The sensor may comprise a plurality of sensors disposed on the tubular prosthesis and spaced a predetermined distance apart from one another, and sensing the stenosis may comprise sensing the stenosis from any position along a length of the tubular prosthesis. The predetermined distance may be approximately 18 cm. Sensing may comprise circumferentially sensing the stenosis with the sensor, and the sensor may be circumferentially disposed around the tubular prosthesis. The tubular prosthesis may be a stent, a graft, or a stent-graft, or any other prosthesis involved in bodily fluid control and management.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 8A-8B 1 show examples of a prosthesis with a plurality of sensors located on the outer wall of the inner lumen, on the outer wall of the outer lumen, and on a combination of those two embodiments which are axially separated from one another.

FIGS. 15-15A show a prosthesis where an open band sensor is disposed on the outer wall of the inner lumen and can be at any angle relative to the longitudinal axis.

FIGS. 16A-16D1 show examples of a prosthesis where an undulating sensor is disposed on either the outer wall of the inner lumen, or on the outer wall of the outer lumen. Other examples show an undulating sensor disposed on either the outer wall of the inner lumen or the outer wall of the outer lumen, which is not fully circumferential.

FIGS. 18A-18D show a prosthesis wherein a sensor forms a closed annular band around either the outer wall of the inner lumen or the outer wall of the outer lumen.

FIGS. 19A-19D show a prosthesis wherein the sensor does not form a complete loop around either the outer wall of the inner lumen or the outer wall of the outer lumen.

DETAILED DESCRIPTION OF THE INVENTION

Figure 1:
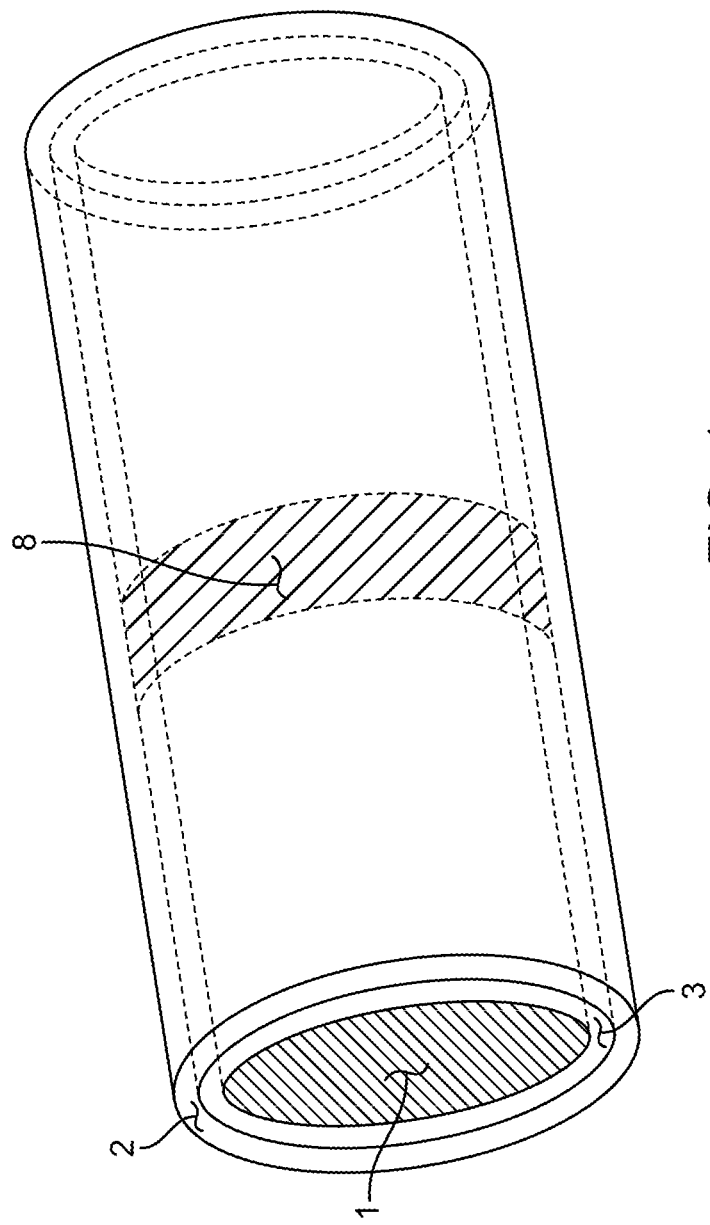
FIG. 1 shows a prosthesis with two lumens and a sensor in between the two lumens.

Specific embodiments of the disclosed device, delivery system, and method will now be described with reference to the drawings. Nothing in this detailed description is intended to imply that any particular component, feature, or step is essential to the invention.

Disclosed herein are exemplary embodiments of methods, systems and devices which allow the medical practitioner to receive various data parameters related to health, noninvasively, after implantation of the measurement device within an animal or person. Without being limited to any specific use the exemplary embodiments of methods, systems and devices disclosed herein relate to measurement of health and functioning of fluid-carrying hollow conduits within an animal or person. Exemplary data parameters being measured by the embodiments disclosed herein may be related to, but not necessarily limited to any of the following: occlusion of the conduit, flow velocity, flow rate, conduit wall thickening, neointimal hyperplasia, and stenosis. One of the exemplary embodiments which will be described herein is a synthetic vascular graft with a sensor that will provide information about blood flow through the graft. Other exemplary embodiments will be described where a sensor is incorporated with other tubular prostheses such as stent-grafts or stents, or grafts based upon natural vessels and/or synthetic vessels based on stem cells.

The device may require a deployment vehicle with a hollow conduit to carry the sensor. This can be accomplished by incorporating the sensor with an expanded polytetrafluoroethylene (ePTFE), PTFE or polyethylene terepthalate vascular graft or as a stand-alone implantable also consisting of ePTFE, PTFE or polyethylene terepthalate. It would also be possible to incorporate the sensor into other types of vascular grafts including autografts, biodegradable grafts, stent-grafts, stents or other prosthetic devices with fluid flowing through the device. In order to prevent biofouling of the present invention; the device may incorporate an anti-fouling coating similar to paclitaxel, ticlodipine, or other therapeutic agents or coatings known in the art.

The sensor will be used to determine the presence, and/or degree, and/or location of abnormal flow patterns, occlusions, flow velocity, flow rate, wall thickening, or stenosis within the hollow conduit. In one exemplary embodiment of this invention, a tactile sensor array utilizing a piezoresistive element, such as polyvinylidene fluoride (PVDF) may be utilized as the sensor. In another exemplary embodiment of this invention, a cilia-like sensor array utilizing PVDF (or similar) is envisioned. The deflection of the PVDF cilia due to blood flow translates into a change in voltage output provided by the sensor. In yet another exemplary embodiment of the invention, the sensor may incorporate biomarker sensing capability. For example, a biomarker for thromboxane A2, an inflammatory mediator present during clot formation.

The voltage change determined by the piezoresistive array may then be transmitted to a low-power application-specific integrated circuit (IC) integrated with the deployment vehicle which converts this data into a flow velocity (emfs) or flow rate (cc/s) upon excitement by an external reader.

An external reader may utilize radiofrequency induction to activate the IC periodically and acquire the flow data. The data would then be transmitted either directly, via an electronic medical record system, or other application to the patient's primary care physician and vascular surgeon. In one embodiment the external reader is a handheld wand or other suitable device which can be activated either automatically or by the user when in proximity to the device and sensor. In another embodiment the reader would be a stand-alone monitor which could periodically interrogate the IC in a user-determined manner either continuously or periodically. Data may be transmitted in any number of ways including via Bluetooth protocols, via the cell phone system, via near field communication, over the Internet, etc.

There are several challenges associated with incorporation of a sensor with a hollow conduit. The sensor is preferably incorporated with the hollow conduit so that it can accurately assess various data parameters relating to flow with little to no disturbance of the fluid flow within the conduit or the ability of the conduit to respond to fluid flow. The sensor also preferably retains its function within the animal or person for an extended period of time, meaning it should be resistant to biofouling. It is also important that the sensor has low immunogenicity so that it causes only minimal immune responses, and avoids causing responses which can result in damage to the host or damage to the device that causes the device to stop working.

An exemplary embodiment of the invention is illustrated in FIG. 1. This embodiment discloses a prosthesis for monitoring a characteristic of flow with the prosthesis comprising a first tubular prosthesis, a second tubular prosthesis having a lumen extending therethrough, wherein the first tubular prosthesis is disposed over the second tubular prosthesis thereby forming a pocket therebetween; and a sensor for detecting a characteristic of fluid flowing through the lumen of the second tubular prosthesis, wherein the sensor is disposed in the pocket, and wherein the sensor is preferably insulated from contact with fluid flowing through the lumen. In the exemplary embodiment displayed in Figure, element 2 represents a hollow conduit that is a tubular prosthesis disposed outside of 3, which represents a hollow conduit that is a tubular prosthesis. Element 1 is the lumen of 3 through which bodily fluids such as blood would preferably flow. Element 8 refers to the sensor element that is detecting a characteristic of fluid flowing through 1.

In other exemplary embodiments the aforementioned hollow conduits may be allograft vessels, xenograft vessels or tubular prostheses such as grafts, stent-grafts or stents made from materials such as ePTFE, PTFE, polyester, polyethylene terephthalate, nitinol, biodegradable materials such as PLA or PGA, or another suitable flexible and/or expandable substrate used as a tubular prosthesis in the body. The aforementioned conduits are preferable for usage in this device because they are commonly used in applications for vascular grafts and have well understood procedures and successful outcomes associated with their use in the body. In addition, one of the two conduits in this exemplary embodiment may also be formed from self-assembled monolayers (SAMs) based on a suitable chemistry such as silane, thiol, or phosphonate. Use of SAMs would preferably enable an easily manufactured conduit to be formed on the inner or outer region of the first conduit.

Tubular prostheses are a preferred embodiment for this device due to the fact that sensor integration with a synthetic conduit will be more desirable than sensor integration with an allograft or xenograft from safety, manufacturing and clinical perspectives. An exemplary embodiment which incorporates a sensor with a tubular prosthesis or prostheses will preferably create little to no increase in immunogenicity in comparison to a simple tubular prosthesis because all of the materials in the device are regarded as foreign by the body's immune system. However, in the exemplary embodiment where a sensor is incorporated with an allograft or xenograft, the immunogenicity of the embodiment may be much greater than a simple allograft or xenograft since the device will have both natural and synthetic materials and the body's immune system will now perceive the entire system to be foreign rather than native. Furthermore, manufacturing processes of tubular prostheses are well understood by those skilled in the art and can be modified more easily for large-scale manufacturing of the exemplary embodiment which incorporates a sensor with tubular prostheses. Also, due to the high clinical failure rate of tubular prostheses, the need for a device enabling monitoring of health parameters relating to flow through a prosthesis is significantly higher than for an allograft or xenograft.

In the aforementioned embodiment (FIG. 1), the sensor would preferably be disposed in a negative space, or pocket between the two conduits. The inner surface of the inner conduit would be in contact with the bodily fluid, and at least partially shield the sensor from direct contact with the bodily fluid, while the outer conduit would preferably limit the sensor's exposure to the body's immune responses that could lead to damage to either the host or device. The configuration in this aspect of the invention preferably enables the sensor to assess parameters relating to patient health including but not limited to non-laminar flow, presence or location of an occlusion, flow rate, flow velocity, pulse rate, conduit wall expansion, conduit wall thickness, or stenosis without significantly interfering with the ability of the hollow conduit to function at an adequate capacity.

The sensor preferably will be able to effectively detect various parameters relating to patient health because energy from fluid flow through the inner conduit would be transmitted to the sensor through the wall of the conduit. Several variations of this arrangement are possible and selection of one or more of these variations can depend on desired features for the particular application. Some of these will be discussed later.

FIGS. 21 and 22 disclose additional exemplary embodiments. The figures disclose examples of a prosthesis for monitoring flow, the prosthesis comprising a first tubular prosthesis having a lumen extending therethrough, a sensor coupled to the first tubular prosthesis, wherein the sensor is configured to sense fluid flow through the lumen; and a layer of material disposed over the sensor and preferably sealingly coupled to a surface of the first tubular prosthesis thereby encapsulating the sensor such that the sensor is insulated from contact with fluid flowing through the lumen.

Figure 21B:
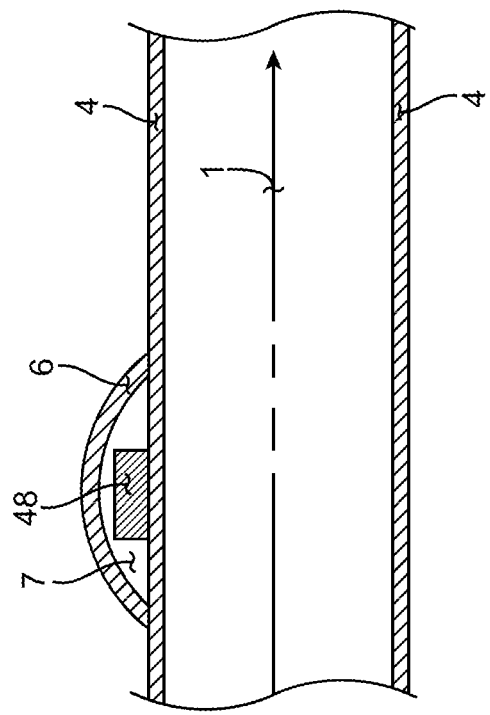
FIGS. 21A-21B show a prosthesis where a sensor is coupled to the inner wall of the inner lumen or the outer wall of the inner lumen.
Figure 21A:
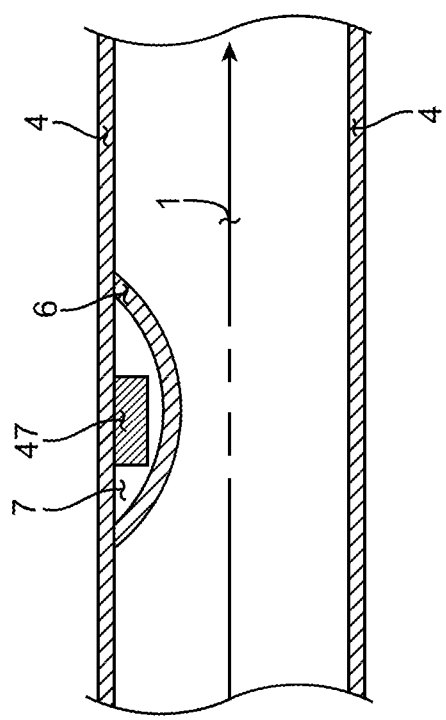
Figure 22A:
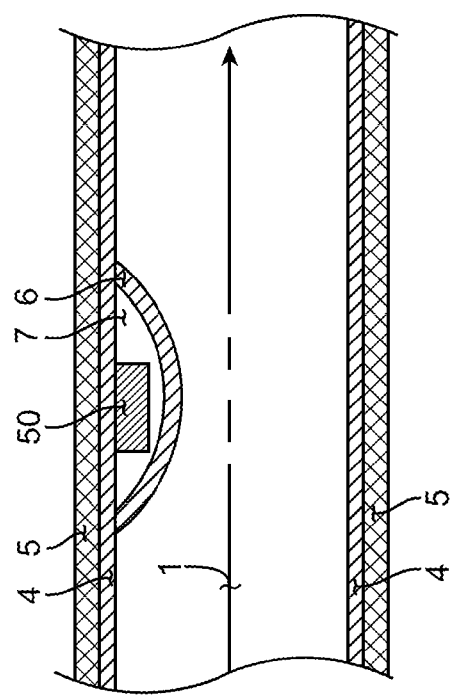
FIGS. 22A-22B show a prosthesis, such as a stent-graft, where a sensor is coupled to the outer wall of the inner lumen or the inner wall of the inner lumen.
Figure 22B:
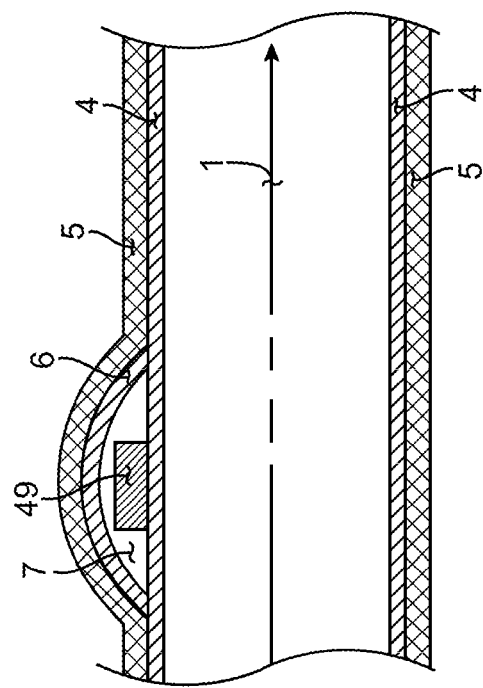

FIG. 21a discloses an exemplary embodiment where a tubular prosthesis 4 has a sensor 47 coupled to the inner surface of 4, or within the lumen of 4. A layer of material 6 is disposed over element 47 and sealingly coupled to the surface of element 4. Depending on the choice of coupling method, material for element 6, sensor size, and other parameters, a pocket 7 may be formed between element 6 and element 47. FIG. 21b discloses another exemplary embodiment, similar to the one disclosed in FIG. 21a, except the sensing element 48 is coupled to the outer surface of element 4 with a layer of material 6 sealingly coupled to the outer surface of element 4. FIG. 22 discloses exemplary embodiments where the tubular prosthesis is a stent graft. As shown in FIG. 22a the sensor element 49 is disposed between the stent 5 and graft 4, coupled with the stent-graft with an additional layer 6 sealingly coupled to element 4. In this embodiment the sensor lies outside of the graft lumen 1. As with FIG. 21, a pocket 7 may be formed depending on the coupling methods between element 6 and element 4 as well as other factors. FIG. 22b is similar to FIG. 22a, except the sensor 50 is coupled to the inner surface of element 4 as opposed to between element 4 and element 6. The key difference between FIG. 22a and FIG. 22b is that the sensor element in 22b is disposed within element 1, the lumen of 4.

In the exemplary embodiments listed above, a sensor element is preferably coupled to a single hollow conduit with an additional layer sealingly coupled over the sensor so it preferably limits exposure of the sensor to bodily fluid and/or tissue. In exemplary embodiments the additional layer may be a patch or a concentric circumferential ring of material. In another exemplary embodiment, the hollow conduit can be an allograft vessel, xenograft vessel, or a tubular prosthesis such as a graft, prosthetic vascular graft, stent-graft or stent made of ePTFE, PTFE, polyester, polyethylene terephthalate, biodegradable materials such as PLA or PGA, or other flexible and/or expandable substrates such as nitinol. The additional layer of material can be made from any number of materials that are biocompatible, flexible, and will not significantly degrade over the lifetime of the device. The fluid flowing through this device in many cases will preferably be a bodily fluid such as blood and the device will be measuring parameters relating to flow of blood through the conduit. It may be beneficial from both a manufacturing and sensor function standpoint to construct this additional layer from the same material that is being used in the hollow conduit. The sensor may see improved functioning from this because of lower impedance mismatch between the sealing layer and the conduit.

Possible materials for the sealing layer include but are not limited to ePTFE, PTFE, polyester, polyethylene terephthalate, nitinol, silicone, polydimethyl siloxane (PDMS), poly vinyl alcohol (PVA), parylene or other thin film polymer coatings. The additional layer may also be constructed from self-assembled monolayers (SAMs) based upon silane, thiol, or phosphonate chemistries. SAM protective layers preferably would produce a minimal feature over the device while being sealingly coupled to the hollow conduit and preferably also provide the necessary protective barrier to limit exposure to tissue and fluids in the body. SAMs preferably would also avoid any potential issues of impedance mismatch from other capping materials or adhesives and also enable easier manufacturing of the device. To potentially minimize the disruption of flow through the hollow conduit, one exemplary embodiment has the sensor coupled to the outer surface of the hollow conduit (sometimes also referred to herein as a tubular prosthesis with a lumen) with the additional layer sealingly coupled over the sensor. In case this embodiment does not produce sufficient sensitivity, an alternative embodiment has the sensor coupled to the inner surface of the hollow conduit with the additional layer sealingly coupled over the sensor.

In one exemplary embodiment with a sensor disposed in a pocket between two hollow conduits such as the embodiment disclosed in FIG. 1, both hollow conduits will be tubular prostheses such as a graft made of a vascular graft material such as ePTFE, PTFE, polyester or polyethylene terepthalate. This embodiment could be especially advantageous for vascular bypass procedures where a clinician needs to repair an obstructed or damaged blood vessel and create a conduit to support blood flow from one region of the body to another. The medical practitioner preferably would be able to surgically place the device into the body as if it were a typical vascular graft. Also, the immune response for such a device preferably would be more easily predictable because the body's fluids and immune system will only be exposed directly to materials that have been rigorously tested for safety and commonly used for implantation over multiple decades.

In another exemplary embodiment of the prosthesis disclosed in FIG. 1, one prosthesis will be made from a vascular graft material such as polyester, ePTFE, PTFE, or Polyethylene terepthalate, or a biodegradable material such as PGA or PLA, while the other prosthesis will be a stent, which can be made from a flexible and/or expandable metallic alloy such as superleastic or shape memory alloys made from nitinol, balloon expandable materials such as stainless steel, cobalt chromium alloy or other metals. The stent may be balloon expandable or self-expanding. This embodiment is advantageous for endovascular procedures and preferably enables the practical application of this sensor into stent-grafts. However, one potential disadvantage of this embodiment may be that the stent prosthesis is known to be very porous and thus may provide minimal protection of the sensor from exposure to the body. Another alternative embodiment that could address this issue will have a sensor disposed between two tubular prostheses made of a vascular graft material such as ePTFE, PTFE, polyester or polyethylene terepthalate. This entire system would then be disposed within or around another tubular prosthesis, such as a stent made from a flexible and/or expandable substrate, such as nitinol, stainless steel or cobalt chromium alloy. This preferably would enable better protection of the sensor by a less porous material than a stent, while still enabling use of this device in stent-grafts. In another exemplary embodiment, the sensor is disposed in a pocket between two hollow conduits, where the inner conduit consists of a naturally occurring vessel found in the body, and the outer conduit can be any suitable protective vessel material, including, but not limited to PTFE, ePTFE, polyester, polyethylene tereptha-late, or a natural cellular barrier. This embodiment could be ideal for venous cuff surgeries which are used to mitigate the immune response to a vascular graft placement in the body. In another exemplary embodiment of the prosthesis disclosed in FIG. 1, the inner conduit consists of a vessel grown outside of the patient's body from stem cells, or another biological source, and the outer conduit can be any suitable protective vessel material, including but not limited to PTFE, ePTFE, polyester, polyethylene terepthalate or a natural cellular barrier.

Figure 23:
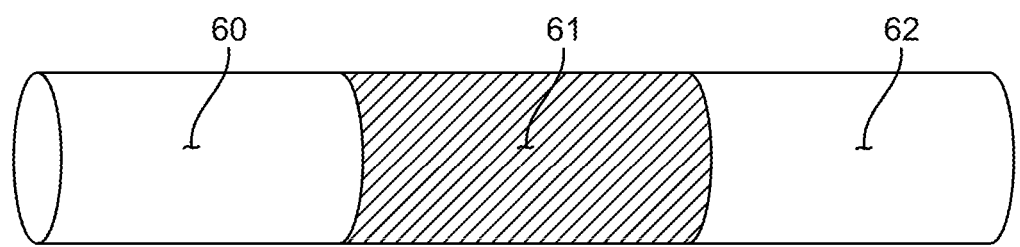
FIG. 23 shows a prosthesis which is attached by end-to-end anastomoses.

In the prostheses disclosed in FIGS. 1, 22, and 23, the nature of the coupling between two conduits, or a conduit and an additional layer can affect a number of aspects of the device, including signal propagation, signal detection, manufacturing, and device lifetime. Several exemplary embodiments of the nature of the coupling would be desirable and all of these mentioned herein may be applied or combined with any of the exemplary embodiments mentioned herein. In one exemplary embodiment some of the desired features are integrally coupled. For the embodiment in FIG. 1, these features are element 2 and element 3, for the embodiments in FIG. 21 and FIG. 22, the preferable features are element 6 and element 4. Integral coupling may minimize potential issues related to interference with signal transduction, and preferably also improve the longevity of the device since no adhesives or sutures are required to maintain the connection between both conduits. One approach for achieving integral coupling is to sinter the features together. In another exemplary embodiment preferred features are fixedly coupled to one another either through a bonding agent, adhesive, or other chemical treatment. This approach may offer benefits for manufacturing while also providing sufficient robustness for long-term stability in the body. In yet another exemplary embodiment, the preferred features may be sutured or stapled together. The benefits of suturing and stapling are that it allows for more easy modification and customization of integration between two conduits or a conduit and an additional layer. This could be especially important during a surgery or other clinical interaction. In addition, sutures and staples are well known to those skilled in the art that are biocompatible, nonimmunogenic, and will robustly survive for long periods of time as an in vivo implant. In another exemplary embodiment both hollow conduits are entirely discrete. This may be advantageous in cases where the dimension or materials chosen for the conduits enable enough mechanical or physical adhesion to preclude any need for adhesive, integral, or other forms of coupling. In an alternative embodiment, the two hollow conduits may be two tubular prostheses that are integral with one another and in which a pocket has been formed to hold the sensor.

Figure 2:
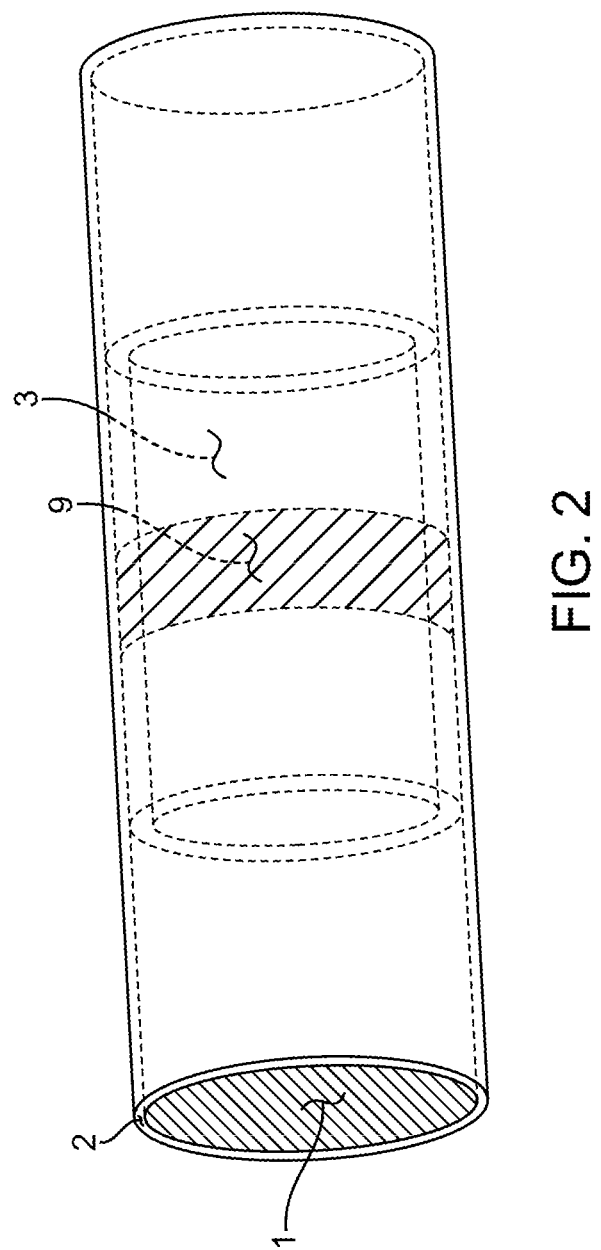
FIG. 2 shows a prosthesis with two lumens with a sensor placed between them in which the inner lumen is substantially shorter than the outer lumen.
Figure 3:
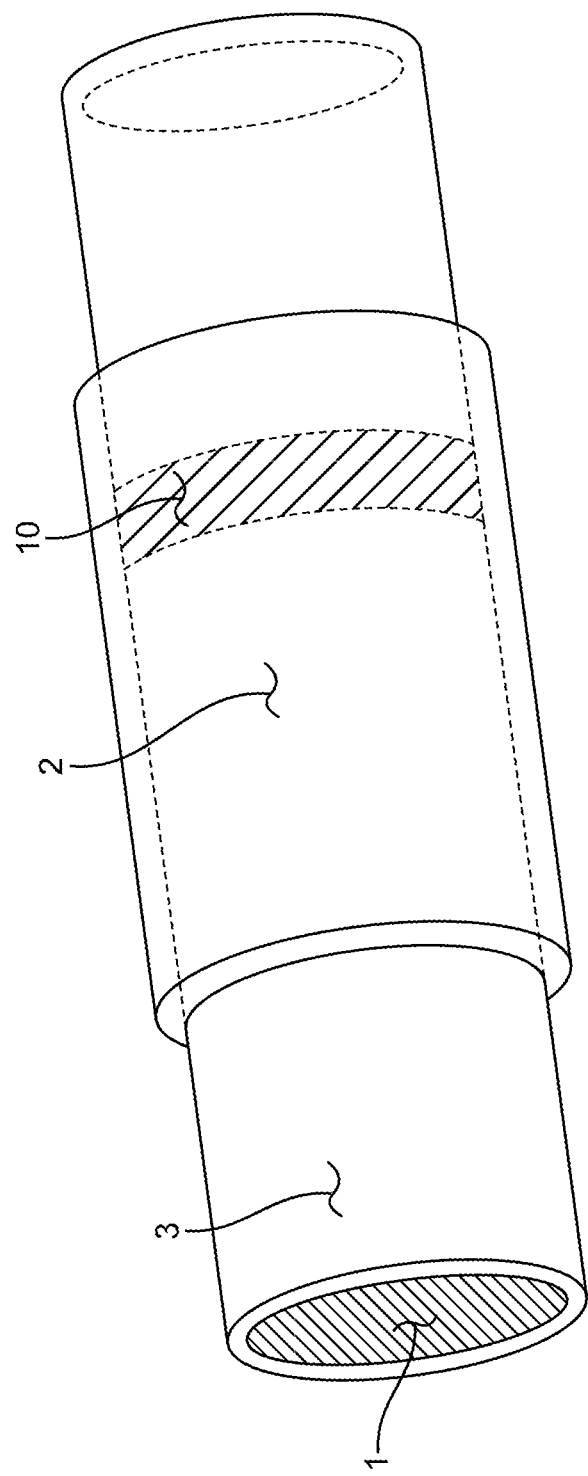
FIG. 3 shows a prosthesis with two lumens with a sensor placed between them in which the outer lumen is substantially shorter than the inner lumen.

FIG. 1 discloses a prosthesis wherein the first tubular prosthesis has a first length and the second tubular prosthesis has a second length substantially the same as the first length. FIG. 2 discloses a prosthesis similar to the one disclosed in FIG. 1 except in FIG. 2 the first tubular prosthesis 2 has a first length and the second tubular prosthesis 3 has a second length shorter than the first length. The sensor 9 is disposed between element 2 and element 3 just as in FIG. 1. FIG. 3 discloses a prosthesis similar to the one disclosed in FIG. 1, except in FIG. 3, the first tubular prosthesis 2 has a first length and the second tubular prosthesis has a second length 3 longer than the first length. The sensor 10 is disposed between element 2 and element 3 just as in FIG. 1.

The exemplary embodiments disclosed in FIGS. 1, 2 and 3 demonstrate that the length of each conduit with respect to the other can be a key aspect to consider in device design. Any of the features of disclosed in exemplary embodiments of this aspect of the invention may be combined with or substituted for any of the features in other exemplary embodiments described herein. The exemplary embodiment of FIG. 1 would enable simpler and more efficient manufacturing of the device and also provide a more complete barrier between the sensor and the surrounding tissue, potentially making the device less immunogenic. The exemplary embodiment disclosed in FIG. 2 reduces the cost of materials for the device because less materials are used per device in comparison to the embodiment where both conduits have identical length.

The exemplary embodiment disclosed in FIG. 3 may be advantageous because of the relatively lower cost of materials in this embodiment, and also because the inner conduit in this embodiment remains undisturbed.

In any of the aforementioned exemplary embodiments, the sensor preferably fulfills several requirements in order to function accurately and to be able to be incorporated successfully with a hollow conduit such as a tubular prosthesis. It is preferably flexible or conformable to a tubular structure, able to respond to acoustic and mechanical signals transmitted through a wall, and also is able to transduce the acoustic/mechanical signals it detects into electrical signals so that the sensor output can be interpreted by an integrated circuit or transmitter. In any embodiment of this device, because it will be a long-term implant in the body and thus, be unable to access a power source easily unless one is implanted into the body, it is desirable for the sensor to be low-power, and ideally, completely passive. Most importantly, the sensor must be able to withstand the conditions in the body over time with minimal drift in the final output and also not be a danger to the person or animal. Because of the specific need for transduction of acoustic/mechanical signals into electrical signals, a piezoelectric sensor would be a likely choice for the sensing element. Use of a piezoelectric sensor also enables the detection and assessment of Doppler signals, which means the piezoelectric element also functions as a Doppler sensor. A polyvinylidine fluoride (PVDF) thin film sensor meets all of the above requirements and is therefore a preferred embodiment of the sensor element in the device. In particular, PVDF film sensors are known to respond to mechanical and acoustic signals with very large electrical signals, even when they are completely passive. This means a PVDF sensor does not draw or require any power at all to function. These capabilities are due to the piezoelectric properties of PVDF which result from the molecular and electron structure that results from well-established manufacturing methods.

These properties enable the sensor to transduce mechanical and acoustic signals into electrical signals without the need for any external power source. PVDF is available in films, and methods are well known to those skilled in the art for fabricating various designs of PVDF film sensors. PVDF film sensor response is also influenced by changes in temperature. Thermal changes can be used to assess a variety of health parameters in a hollow conduit including but not limited to non-laminar flow, occlusion, flow rate, flow velocity, wall thickening, or stenosis. PVDF film sensors also operate across a very wide band of frequency ranges, meaning that very low frequency and high frequency signals can be detected with these sensors. Another feature of PVDF film sensors that could beneficial to the device is their ability to act as a source for energy harvesting from the body. Since PVDF films are able to translate mechanical energy into electrical energy in a passive manner, energy harvesting systems which are known to those skilled in the art, may be constructed to help offset the power requirements of other components in the device.

A PVDF film sensor deployed with a hollow conduit can be used to detect a variety of signals relating to the subject's health. In the exemplary embodiments described above where a PVDF film sensor is incorporated with one or more hollow conduits such as a xenograft, allograft, or tubular prosthesis such as a graft, stent, or stent-graft, the sensor can detect a number of parameters which ultimately relate to both subject health and fluid flow. The PVDF sensor can detect mechanical signals exerted by fluid flowing through the conduit such as strain, stress, or pressure. The PVDF sensor will also respond to acoustic signals generated by fluid flowing through the conduit. As mentioned earlier, the PVDF sensor will also be responsive to thermal changes. Taken individually or together these parameters enable the detection of various parameters that are critical to subject health including but not limited to flow velocity (emfs), flow rate (volumetric), stenosis, wall thickness, flow turbulence, non-laminar flow, occlusion, level of occlusion or occlusion location. For an exemplary embodiment where the hollow conduit is a tubular prosthesis that is utilized for blood flow, the ability to detect flow velocity, flow rate, level of occlusion and/or occlusion location are particularly valuable. Experiments have been conducted with this embodiment to determine whether it could be used to assess these and other health parameters relating to blood flow through a vascular graft. The experiments suggest that such an embodiment can successfully determine occlusion level, flow rate, flow velocity and location of an occlusion utilizing the PVDF sensor's ability to detect pressure and acoustic signals. The experiment and results are described briefly below.

Experimental Results

Experiments were conducted with a PVDF film sensor incorporated with an ePTFE vascular graft with an additional layer sealingly coupled over the sensor. Biological fluid flow was simulated by attaching the vascular graft to a Harvard Apparatus large animal heart pump and pumping water and blood mimicking fluid (ATS Medical) through the system. The system was implanted into ballistics gel to mimic an in vivo tissue environment. Constrictions were applied upstream and downstream of the PVDF sensor to determine its ability to respond to occlusions in the flow. Stroke volume, heart rate, and diastole/systole ratio were varied on the pump to determine the device's ability to detect various parameters relating to flow and the graft. Through these experiments, it was determined that the device is able to detect changes in flow rate, flow velocity, the level of occlusion, the location of an occlusion, and turbulence of flow.

Several possible sensor configurations can exist in the embodiments described above where a PVDF sensor is incorporated with one or more hollow conduits and the exemplary embodiments of sensor configurations described herein may be incorporated with one or more hollow conduits in any of the exemplary embodiments mentioned herein. As mentioned earlier, these hollow conduits may be allograft vessels, xenograft vessels or tubular prostheses such as grafts or stents made from materials such as ePTFE, PTFE, polyester, polyethylene terephthalate, biodegradable materials, nitinol, or another suitable flexible and/or expandable substrate used as a tubular prosthetic in the body. A plurality of individual sensor embodiments or some combination of the sensor embodiments mentioned herein may be used in the device. Different configurations of a PVDF sensor will result in different sensor responses due to PVDF film orientation, pattern and shape. This is because piezoelectric PVDF films are axially oriented and provide a differential electrical response in each axis. For the purposes of this discussion the "x-axis" will be used to refer to the most sensitive axis of the PVDF film sensor.

PVDF film sensors may be utilized as sensor elements in some or all of the exemplary embodiments described herein. In one exemplary embodiment the x-axis of the sensor will be oriented parallel to the longitudinal axis of the hollow conduit(s). When oriented in this fashion, the sensor will be more sensitive to mechanical and acoustic waves propagating lengthwise down the longitudinal axis of the hollow conduit. In another exemplary embodiment the x-axis of the PVDF sensor will be perpendicular to the longitudinal axis of the hollow conduit(s) and thus be disposed circumferentially around either hollow conduit. This enables the sensor to be more sensitive to mechanical and acoustic signals directed perpendicularly from the circumferential axis of the hollow conduit. Through experimentation, this has been determined to be the preferred orientation of the PVDF film for sensitivity to fluid flow through a graft. This is due to the fact that circumferentially oriented strains and acoustic signals are more correlated to fluid flow rates and characteristics through the graft than longitudinally oriented signals. Longitudinally oriented signals appear to be more a function of heart rate than fluid flow properties. Another exemplary embodiment which would allow simultaneous measurement of both longitudinally and circumferentially oriented signals is a sensor which is oriented at an angle or transverse to the longitudinal axis of the hollow conduit(s). The sensor could be interrogated in such a way that flow, pulse, and other data signals can be collected during data analysis from a single sensor. In another exemplary embodiment, a plurality of sensors are disposed circumferentially around one or more hollow conduits with the x-axis of each sensor aligned identically with relation to the longitudinal axis of the hollow conduit. In this embodiment, comparison of sensor responses at different locations in the hollow conduit could be useful for assessing changes in various data parameters of interest that have been mentioned herein. This embodiment in particular is useful for assessing changes in various data parameters as a function of location since the sensor would be oriented and disposed in a similar fashion with the conduit at various locations. In another exemplary embodiment a plurality of sensors wherein each sensor is disposed differentially from the other with respect to their orientation with the longitudinal axis of the hollow conduit(s). The benefit of this embodiment is that it will be possible to assess various distinct data parameters from a dedicated sensor for each parameter. For example, one sensor may be disposed circumferentially around a hollow conduit with the x-axis of the PVDF film sensor being perpendicular to the longitudinal axis, while a second sensor is disposed in such a manner that the x-axis of the PVDF film is parallel to the longitudinal axis. This would enable detection of both longitudinally and circumferentially oriented signals from the hollow conduit with a dedicated sensor for each type of signal. In another exemplary embodiment, a plurality of sensors exists wherein each sensor is disposed differentially from the other with respect to their orientation with the longitudinal axis of the hollow conduit (s) and each sensor is helically incorporated with the hollow conduit(s) such that a length of the conduit(s) has multiple helical sensors. This embodiment would enable detection of multiple parameters as well as assessment of changes of each parameter with respect to location over a length of the conduit. Another exemplary embodiment with a PVDF sensor disposed between two hollow conduits would have the PVDF sensor forming a serpentine pattern around the inner conduit. This would essentially orient the film in both the longitudinal and circumferential axes at various points around the serpentine pattern, and thus both capture signal in the longitudinal axis as well as the circumferential while still allowing expansion of the conduit, thus not interfering with its functionality. Finally, in another exemplary embodiment the PVDF sensor forms a candy-stripe pattern around the inner conduit. This last pattern would allow for signal to be obtained from both the longitudinal and circumferential axes. While some signal in each would be lost, it would also allow for any time varying parameters associated with flow to be obtained. Such parameters may include the transit time of a pulse between the two candy stripes or the phase shift of a pulse between the two candy stripes. Using a plurality of any of the aforementioned sensors enables the interrogation of multiple parameters relating to flow at once. In addition, multiple sensors can be used to perform transit time measurements in alternative embodiments.

Another key aspect to consider for a PVDF sensor incorporated with any of the exemplary embodiments described herein is shape and coverage of the sensor on the hollow conduit. This can affect function and sensitivity of the device. In one exemplary embodiment the PVDF sensor forms a complete loop around the circumference of the outer or inner wall of a hollow conduit. This maximizes the ability of the sensor to respond to circumferentially oriented signals. However, this embodiment also has the potential to constrict expansion of the inner conduit, which may adversely affect the conduit and its ability to sustain healthy, normal fluid flow. Another exemplary embodiment that can address this issue consists of a PVDF sensor which covers <360 degrees of the circumference of the outer or inner wall of a hollow conduit. While part of the circumferentially oriented signals may be lost or the signal may be reduced in strength, in this embodiment the conduit can more easily expand in response to fluid flow. In another exemplary embodiment, the PVDF film sensor will cover about 170-190 degrees of the circumference of one or more hollow conduits with the x-axis of the sensor being oriented circumferentially with respect to the conduit.

The advantage of this embodiment is that when a PVDF film sensor covers roughly half the circumference of a hollow conduit, it maximizes the stretch that the sensor would undergo as a result of circumferential signals for sensor configurations where the film does not cover the full circumference of a conduit.

Figure 4:
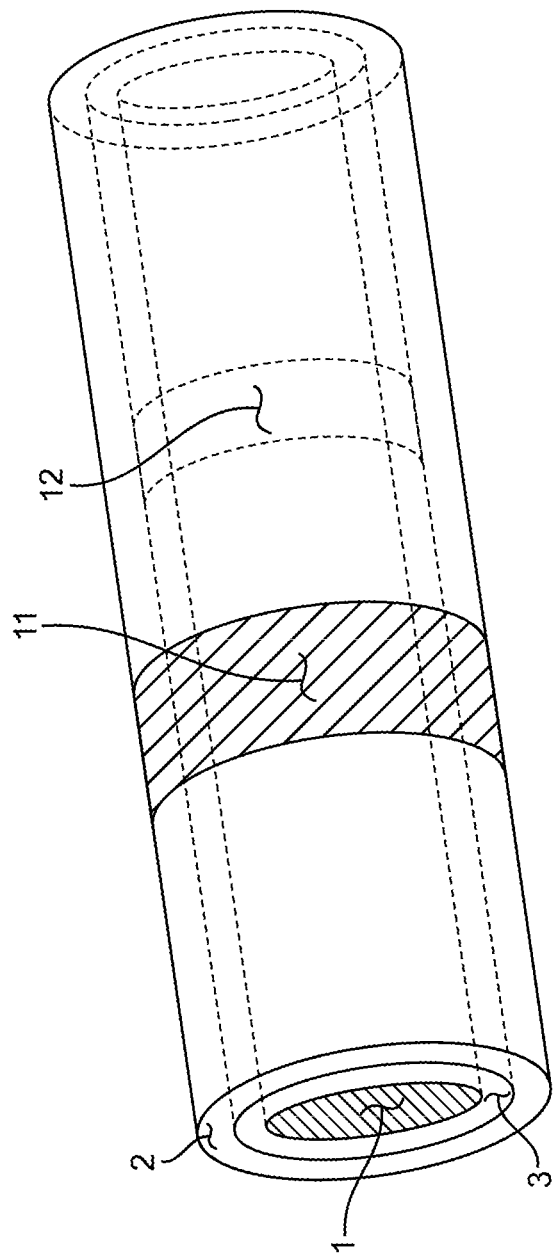
FIG. 4 shows a prosthesis with two lumens in which one sensor is placed between the two lumens on the inner lumen, and one sensor is placed on the outside of the outer lumen.

FIG. 4 discloses an exemplary embodiment of the prosthesis disclosed in FIG. 1 wherein the sensor is disposed circumferentially around the first and/or second tubular prosthesis. Element 11 is a sensor which is coupled around the first tubular prosthesis 2, while element 12 is a sensor coupled around the second tubular prosthesis 3. In the case of the PVDF film sensor mentioned herein, the x-axis of the sensor would be oriented circumferentially to enhance sensitivity to circumferentially oriented signals resultant from flow. Examples of these signals are pressure, wall expansion, etc. Other exemplary embodiments relating to FIG. 4 may include one or both sensors in various configurations and combinations with other exemplary embodiments disclosed herein. To maximize sensitivity to circumferentially oriented signals, the sensor in FIG. 4 can be oriented orthogonally to the longitudinal axis of 2 or 3. If sensitivity to both circumferentially oriented and longitudinally oriented signals is desired the sensor in FIG. 4 would be circumferentially disposed but, not orthogonally to the longitudinal axis of element 2 or element 3.

Figure 5A:
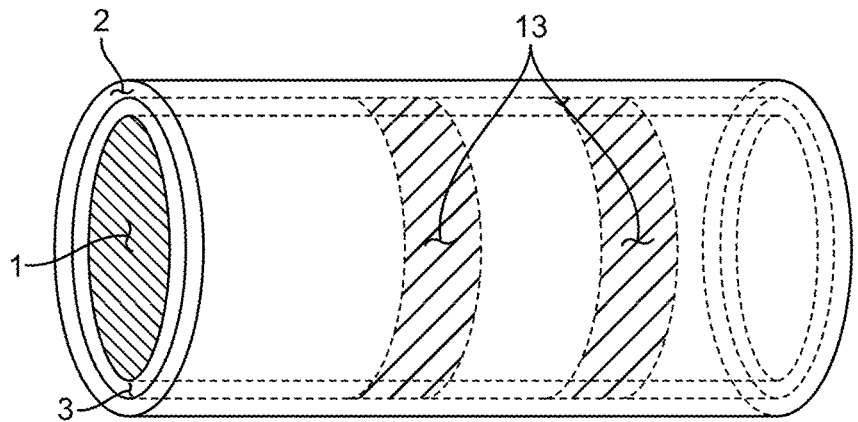
FIGS. 5A-5C show examples of a prosthesis with a plurality of sensors located on the outer wall of the inner lumen, on the outer wall of the outer lumen, and on a combination of those two cases which are disposed circumferentially.
Figure 5B:
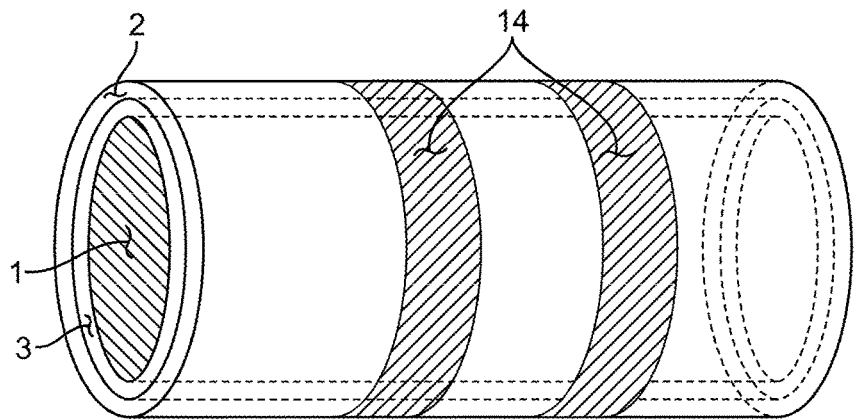
Figure 5C:
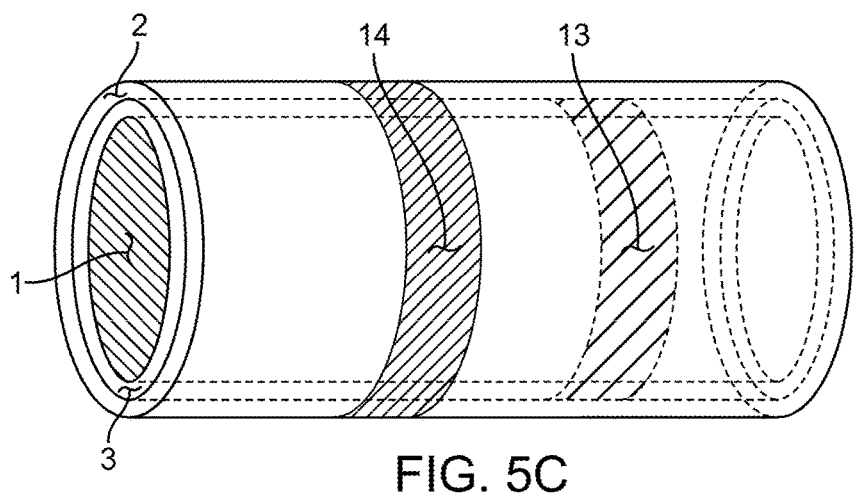

FIG. 5 discloses exemplary embodiments of FIG. 1 wherein the sensor comprises a plurality of sensors disposed circumferentially around the first and/or the second tubular prosthesis. In FIG. 5a two circumferentially oriented sensing elements 13 are disposed around the second prosthesis 3 and within the first prosthesis 2. In FIG. 5b, two circumferentially oriented sensing elements 14 are disposed around the first prosthesis 2. In FIG. 5c, two circumferentially oriented sensing elements are depicted with one sensor 14 being disposed around the first prosthesis 2 and the second sensor 13 being disposed around the second prosthesis 3 and within the first prosthesis 2. The benefits of using a plurality of sensors is manifold. Redundancy is a desirable characteristic for any sensing system that will be used in the body. In addition, when using multiple sensors, transit time measurements may be performed to assess characteristics relating to flow. A plurality of sensors preferably also enables measurement of various parameters at various locations along the prosthesis. Various combinations of the embodiments disclosed in FIGS. 5a, 5b, and 5c are possible both with each other and with other exemplary embodiments disclosed herein.

Figure 6A:
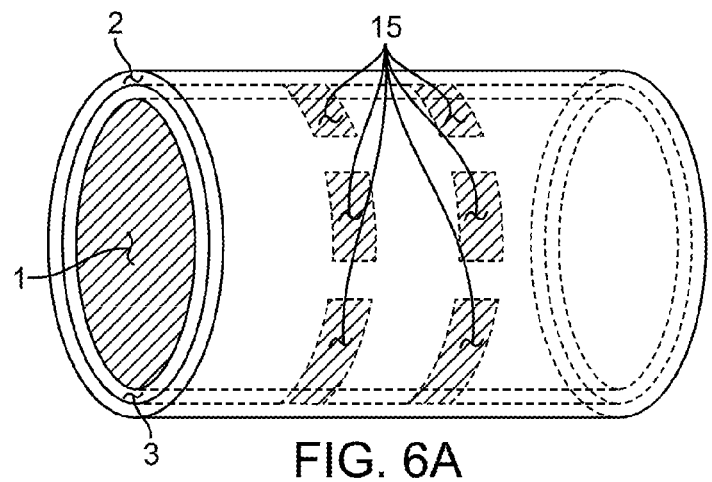
FIGS. 6A-6C show examples of a prosthesis with a plurality of sensors located on the outer wall of the inner lumen, on the outer wall of the outer lumen, and on a combination of those two cases wherein the sensors are located at different locations on the longitudinal axis. The sensors further comprise a plurality of sensors along a common plane.
Figure 6B:
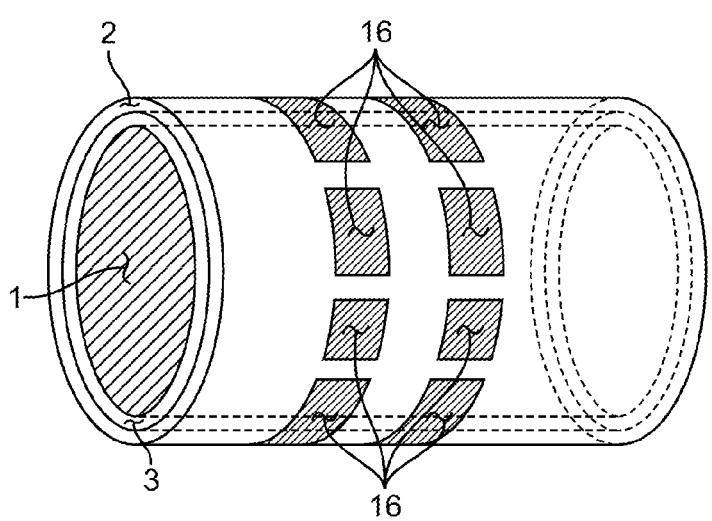
Figure 6C:
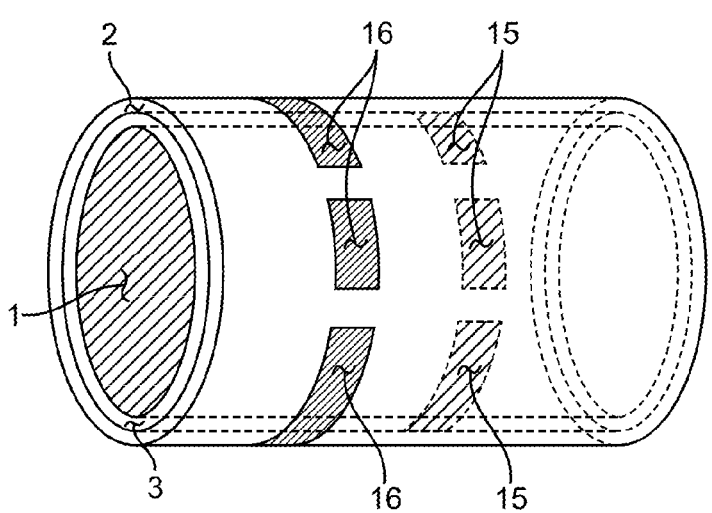

FIG. 6 discloses exemplary embodiments of the prosthesis of FIG. 1 wherein the sensor comprises a plurality of discrete sensors disposed circumferentially along the first and/or the second tubular prosthesis. In FIG. 6a two rings of multiple discrete sensors 15 are disposed circumferentially around the second prosthesis 3 and within the first prosthesis 2. In FIG. 6b two rings of multiple discrete sensors 16 are disposed circumferentially around the first tubular prosthesis 2. In FIG. 6c two rings of multiple discrete sensors are depicted with one ring of multiple discrete sensors 16 disposed circumferentially around the first tubular prosthesis 2 and a second ring of multiple discrete sensors 15 disposed circumferentially around the second tubular prosthesis 3 and within the first tubular prosthesis 2. The exemplary embodiments disclosed in FIG. 6 may be used in combination with any of the exemplary embodiments described herein. The benefit of using multiple discrete sensors in a circumferentially oriented ring is that measurement of circumferentially oriented signals related to flow is still possible in these exemplary embodiments, but now the variation and changes in signal along the circumferential axis can be measured. This could be desirable in vascular applications in terms of assessing non-uniformity of flow or development of abnormalities in the lumen 1 of the tubular prosthesis since blockages can form at one point location along a circumference, rather than uniformly around an entire circumference of the prosthesis.

Figure 7A:
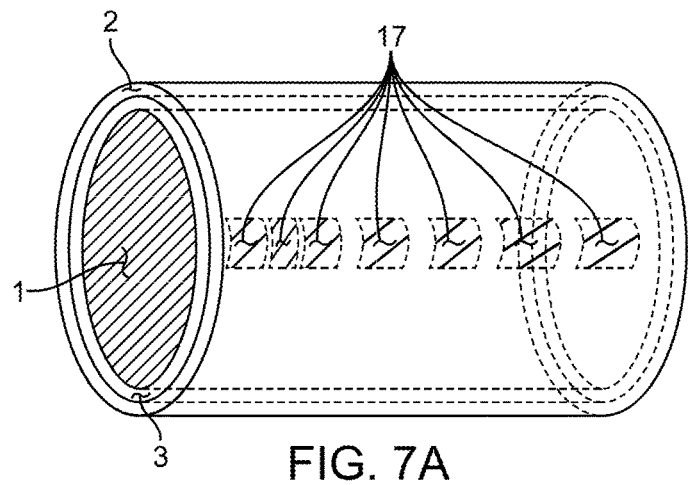
FIGS. 7A-7C show examples of a prosthesis that has a plurality of sensors located on the outer wall of the inner lumen, on the outer wall of the outer lumen, and on a combination of those two embodiments which further contain multiple sensors which are disposed axially.
Figure 7B:
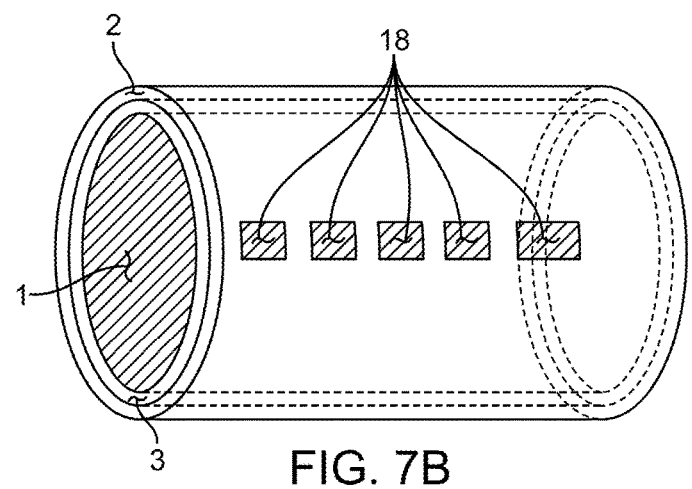
Figure 7C:
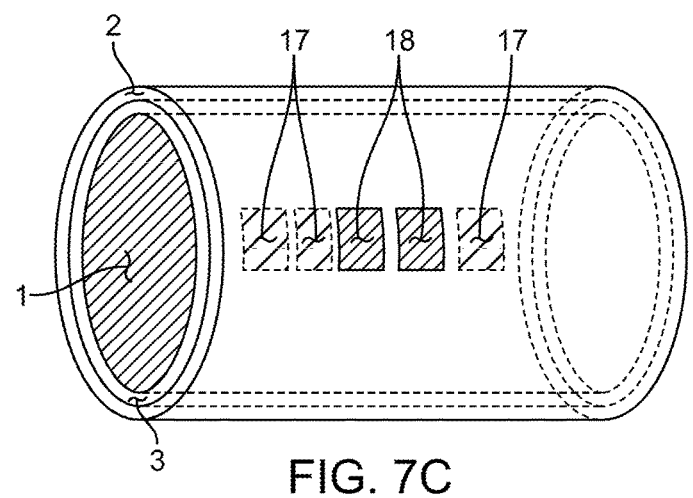

FIG. 7 discloses exemplary embodiments of FIG. 1 wherein the sensor comprises a plurality of discrete sensors disposed axially along the first and/or the second tubular prosthesis. In FIG. 7a a plurality of discrete sensors 17 are disposed axially along the outer surface of the second prosthesis 3 and within the first prosthesis 2. In FIG. 7b a plurality of discrete sensors 18 are disposed axially along the outer surface of the first prosthesis 2. In FIG. 7c one plurality of discrete sensors 18 are disposed axially along the outer surface of the first prosthesis 2 and another plurality of discrete sensors 17 are disposed axially along the outer surface of the second prosthesis 3 and within the first prosthesis 2. The exemplary embodiments disclosed in FIG. 7 may be used in combination with any of the other exemplary embodiments described herein. In the embodiments described in FIG. 7, the plurality of axially disposed sensors may be disposed parallel to the longitudinal axis of the prosthesis or they may not be. If they are disposed substantially parallel to the longitudinal axis of the prosthesis, the sensors preferably will be able to respond most sensitively to longitudinally directed signals. If they are disposed in such a manner that they are not substantially parallel to the longitudinal axis of the graft, they preferably will be able to respond sensitively to both longitudinal and circumferentially directed signals.

The embodiments described in FIG. 7 are desirable because they may enable assessment of parameters related to the flow at discrete locations along the length of a tubular prosthesis. This could be helpful in identifying vulnerable locations along the length of the prosthesis and guide intervention decisions for clinicians.

FIG. 8 discloses exemplary embodiments of the prosthesis disclosed in FIG. 1, wherein the sensor comprises first and second annular bands circumferentially disposed around the first and/or the second tubular prosthesis, and wherein the first annular band is axially separated from the second annular band. In FIG. 8a two annular band sensors 19 are circumferentially disposed around the first prosthesis 2 and axially separated from one another. In FIG. 8b two annular band sensors 19 are circumferentially disposed around the second prosthesis 3 and within the first prosthesis 2 and axially separated from one another. In another exemplary embodiment either or both of the annular band sensors form a closed loop around one of the prosthesis (either element 2 or element 3). The exemplary embodiments disclosed in FIG. 8 may be used in combination with any of the other exemplary embodiments described herein. The embodiments described by FIG. 8 are desirable since multiple sensor elements may allow for simultaneous measurement of different parameters. This preferably allows for transit time measurements as well as measurement of various locations along the length of a tubular prosthesis. In particular, two sensors may be very desirable because they will likely have a lower power and processing footprint than other multi-sensor embodiments while preferably still offering much of the same functionality specifically for transit time measurements.

Figure 9A:
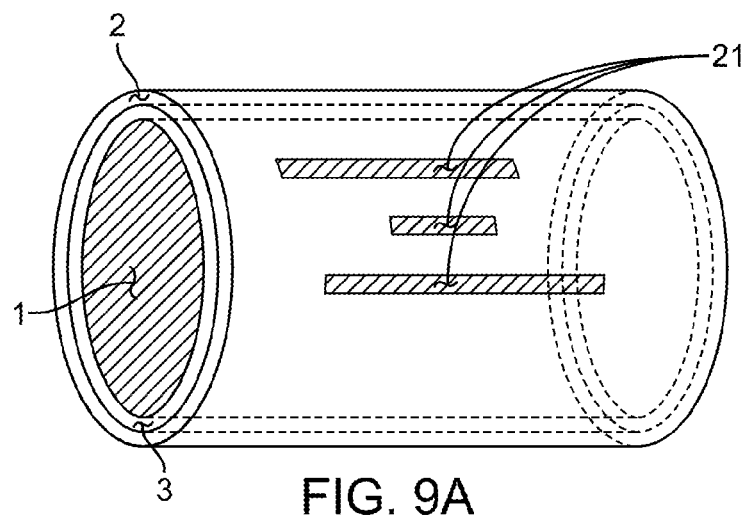
FIGS. 9A-9B show a prosthesis containing a number of elongated sensors on either the outer wall of the inner lumen or the outer wall of the outer lumen wherein these sensors are arrayed circumferentially around the graft.
Figure 9B:
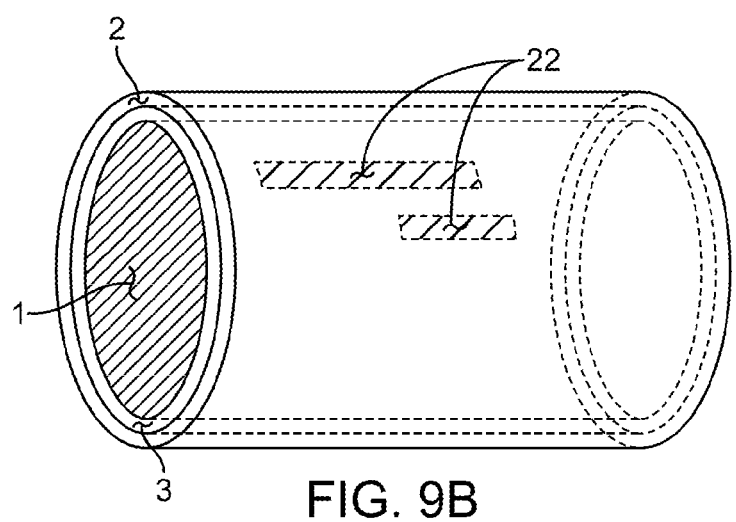
Figure 10:
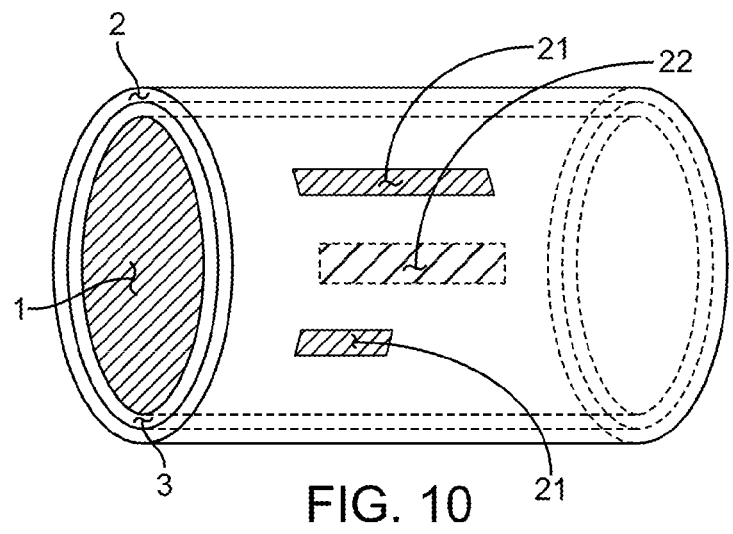
FIG. 10 shows a prosthesis containing a number of elongated sensors on either the outer wall of the inner or the outer wall of the outer lumen or some combination thereof wherein these sensors are arrayed circumferentially around the graft.

FIGS. 9 and 10 disclose exemplary embodiments of the prosthesis disclosed in FIG. 1, wherein the sensor comprises a plurality of elongated sensors, the plurality of elongated sensors axially oriented along the first and/or the second tubular prosthesis. In FIG. 9a a plurality of elongated sensors axially oriented and of different dimensions 21 are disposed on the outside of the first prosthesis 2. In FIG. 9b a plurality of elongated sensors axially oriented and of different dimensions 22 are disposed on the outside of the second prosthesis 3 and within the first prosthesis 2. In FIG. 9c one plurality of elongated sensors axially oriented and of different dimension 21 are disposed on the outside of the first prosthesis 2 and a single, axially oriented elongated sensor 22 is disposed on the outside of the second prosthesis 3 and within the first prosthesis 2. The exemplary embodiments disclosed in FIGS. 9 and 10 may be used in combination with any of the other exemplary embodiments described herein. The embodiments described by FIGS. 9 and 10 are desirable because they preferably allow multiple signals that are associated with the longitudinal stretching of the graft to be interrogated simultaneously at different discrete lengths along the graft. The analysis of signal propagation along different lengths of sensor at different locations would preferably allow for a more complete analysis of fluid flow through the prosthesis. Further, if the sensors are located longitudinally along the graft at different locations and at different angles to one another, this also preferably allows the procurement of different components of the base signal.

Figure 11A:
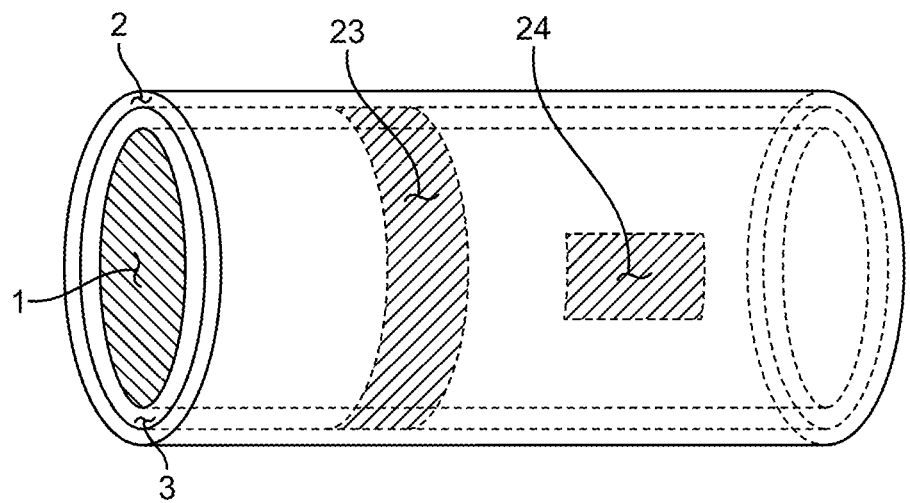
FIGS. 11A-11B show examples of a prosthesis with a plurality of sensors located on the outer wall of the inner lumen, on the outer wall of the outer lumen, where the sensors have different orientations.
Figure 11B:
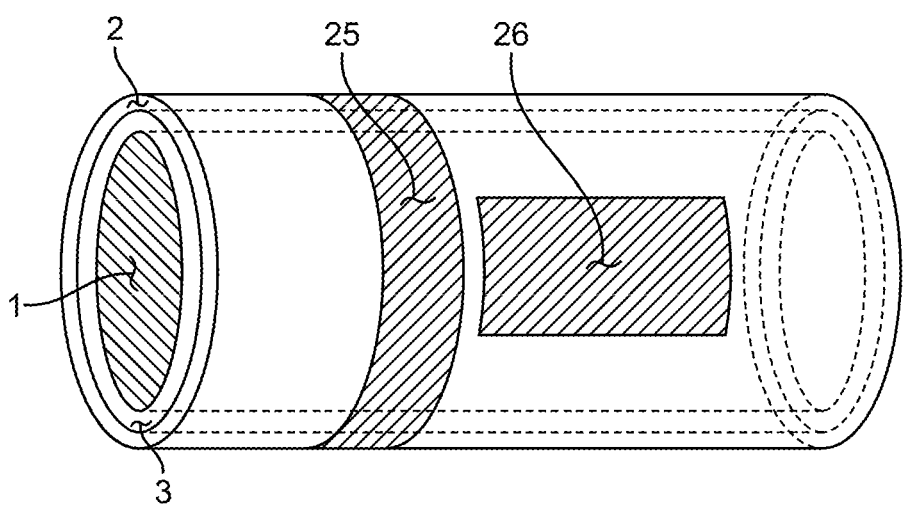
Figure 12:
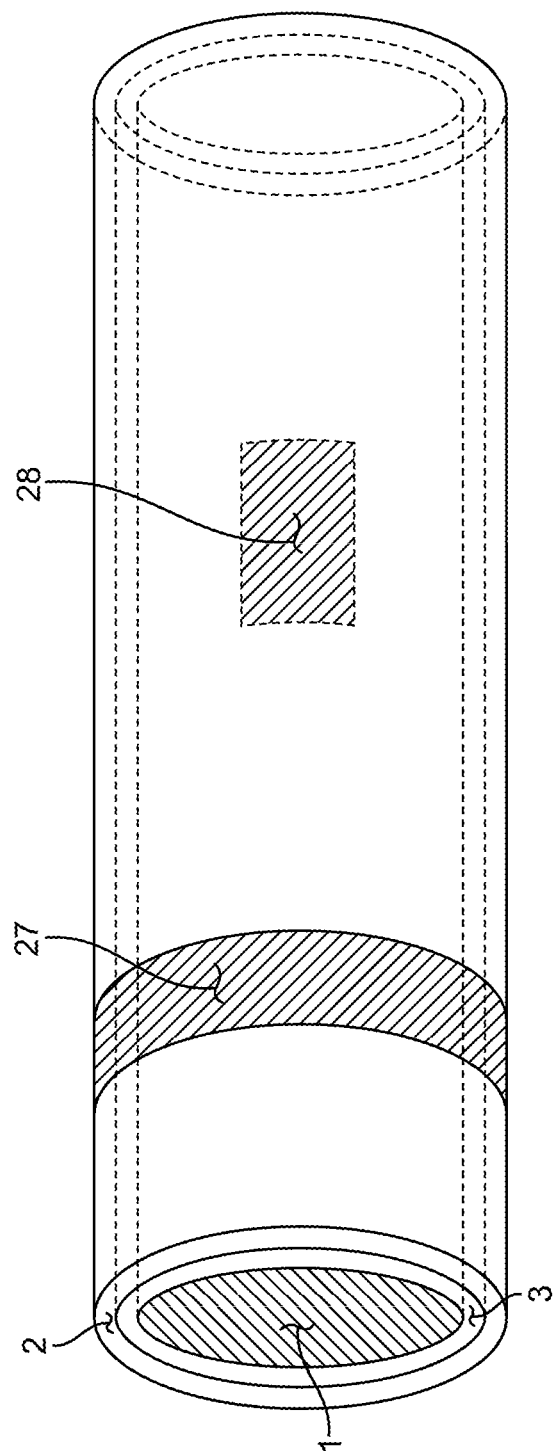
FIG. 12 shows a prosthesis where sensors of different orientations may be on either the outer wall of the inner lumen, or the outer wall of the outer lumen or some combination thereof.

FIGS. 11 and 12 disclose exemplary embodiments of the prosthesis in FIG. 1 wherein the sensor comprises two sensors wherein the first sensor is configured to capture a first characteristic of the fluid flow in the lumen, and wherein the second sensor is configured to capture a second characteristic of the fluid flow in the lumen and wherein the first sensor is disposed in a first orientation relative to the first or the second tubular prosthesis, and wherein the second sensor is disposed in a second orientation relative to the first or the second tubular prosthesis, and wherein the first orientation is different than the second orientation. In FIG. 11a a first sensor 23 is oriented orthogonally to the longitudinal axis of the prosthesis while a second sensor 24 is oriented parallel to the longitudinal axis of the prosthesis. Both 23 and 24 are disposed outside of the second prosthesis 3 and within the first prosthesis 2. In FIG. 11b a first sensor 25 is oriented orthogonally to the longitudinal axis of the prosthesis while a second sensor 26 is oriented parallel to the longitudinal axis of the prosthesis. Both 25 and 26 are disposed outside of the first prosthesis 2. In FIG. 12 a first sensor 27 is oriented orthogonally to the longitudinal axis of the prosthesis and disposed outside of the first prosthesis 2. A second sensor is oriented parallel to the longitudinal axis of the prosthesis and disposed outside of the second prosthesis 3 and within the first prosthesis 2. The exemplary embodiments disclosed in FIGS. 11 and 12 may be used in combination with any of the other exemplary embodiments described herein. The embodiments described by FIG. 11 are desirable because they preferably allow for nearly pure components of both the stretching of the prosthesis longitudinally and the outward "bulging" of the prosthesis to be measured simultaneously. By orienting the sensors in this fashion, it will preferably not require significant signal de-convolution between the "bulging" aspect of fluid flow through the prosthesis and the longitudinal stretching of the prosthesis. As an added benefit, orienting the two sensors on the same lumen (element 2 or element 3) may yield less noisy data as compared to sensors that are on two different lumens (elements 2 and element 3). The embodiments described by FIG. 12 are desirable because they preferably allow for nearly pure components of both the stretching of the prosthesis longitudinally and the outward "bulging" of the prosthesis to be measured simultaneously. As an added benefit, measuring in two planes (one or more sensors on element 2 and one or more sensors on element 3) may preferentially be immune to any localized stiffening effects that are caused by having two sensors in close proximity on the same plane (two sensors on element 2 or element 3).

Figure 13A:
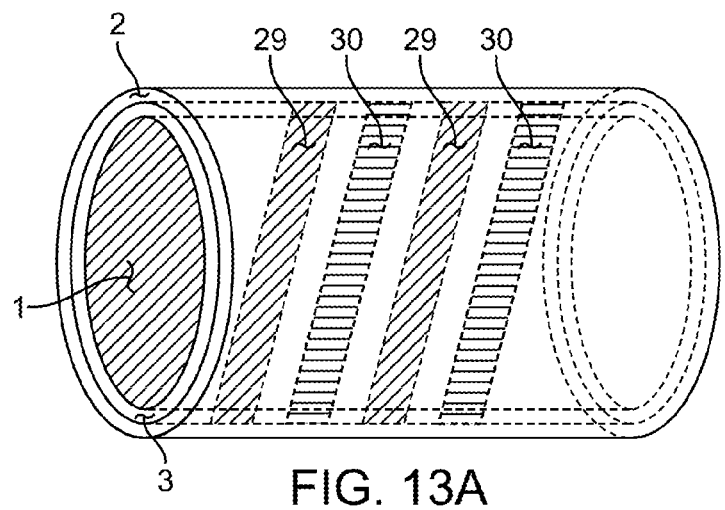
FIGS. 13A-13C shows examples of a prosthesis with a plurality of helically disposed sensors located on the outer wall of the inner lumen, on the outer wall of the outer lumen, and on a combination of those two cases, which are axially separated from each other.
Figure 13B:
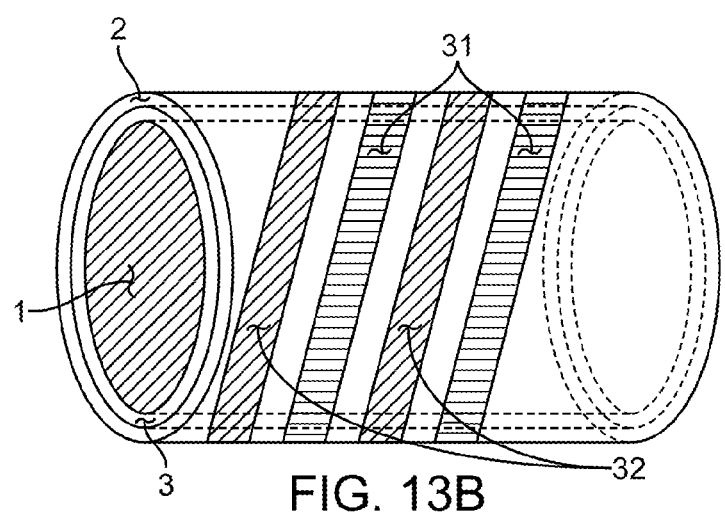
Figure 13C:
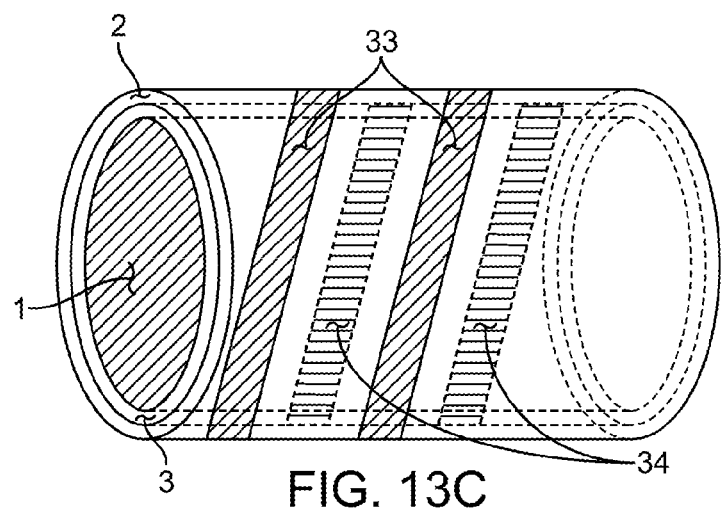

FIG. 13 discloses an exemplary embodiment of the prosthesis from FIG. 1 wherein the sensor comprises a plurality of sensors wherein the plurality of sensors are helically disposed around the first or the second tubular prosthesis. In FIG. 13a a first sensor 29 is helically disposed over a length of the prosthesis, disposed over the second prosthesis 3 and within the first prosthesis 2. A second sensor 30 is helically disposed over a length of the prosthesis, does not intersect with 29, is disposed over the second prosthesis 3 and within the first prosthesis 2. In FIG. 13b a first sensor 31 is helically disposed over a length of the prosthesis and disposed over the first prosthesis 2. A second sensor 32 is helically disposed over a length of the prosthesis, does not intersect with 31 and is disposed over the first prosthesis 2. In FIG. 13c a first sensor 33 is helically disposed over a length of the prosthesis 2 and is disposed over the first prosthesis 2. A second sensor 34 is helically disposed over a length of the prosthesis, does not intersect with 33, is disposed over the second prosthesis 3 and within the first prosthesis 2. The exemplary embodiments disclosed in FIG. 13 may be used in combination with any of the other exemplary embodiments described herein. The embodiments described by FIG. 13 are desirable because they can preferably capture multiple components of the signal of interest with the same sensor (e.g. stretch and bulging) while not constraining the bulging as much as a closed annular band nor while not only sensing the stretching component like a sensor parallel to the longitudinal axis would. As an added benefit, because there are two sensors (e.g. 29 and 30) that follow one another around the lumen but are spatially different, they are preferably also able to measure any travel time dependent signal.

Figure 14:
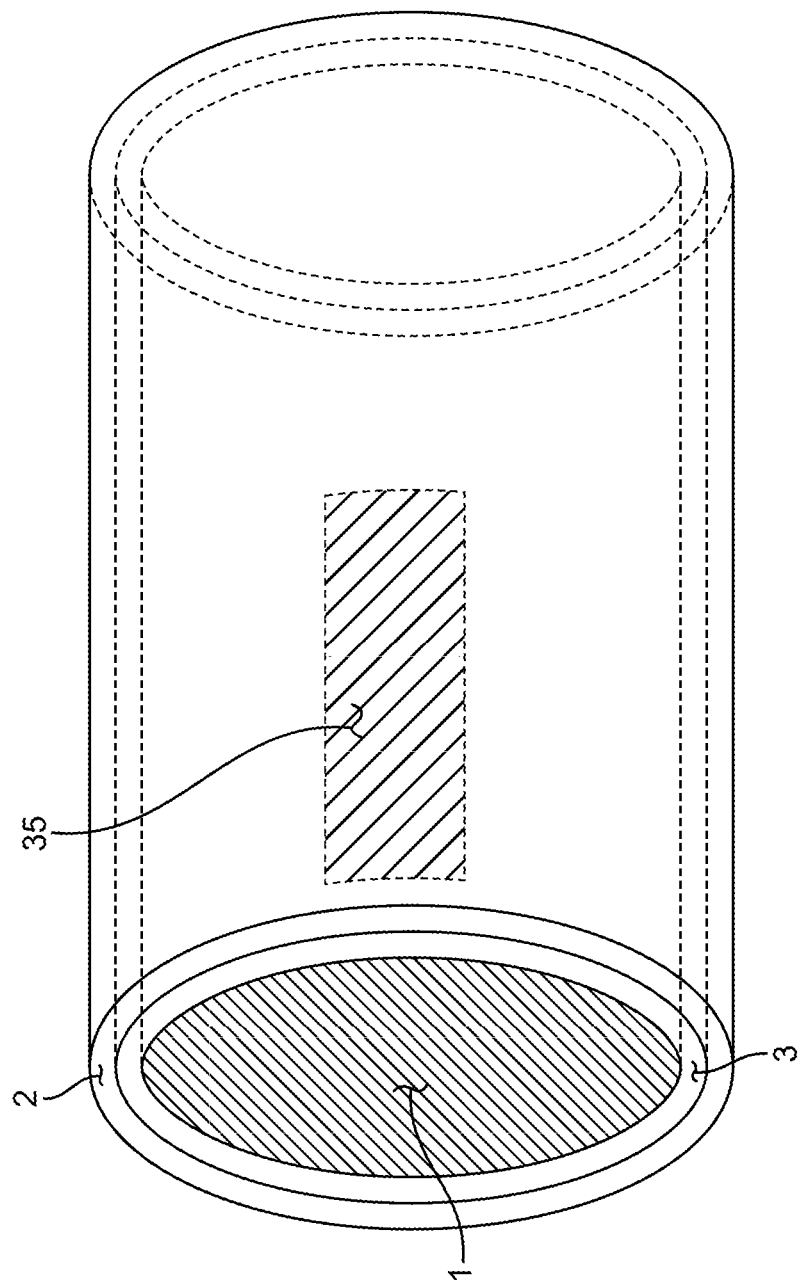
FIG. 14 shows a prosthesis where a sensor which is substantially parallel to the longitudinal axis may be disposed on either the outer wall of the inner lumen or on the outer wall of the outer lumen.

FIG. 14 discloses an exemplary embodiment of the prosthesis disclosed in FIG. 1 wherein the first or the second tubular prosthesis has a longitudinal axis, and wherein the sensor is disposed substantially parallel to the longitudinal axis. The sensor element 35 is disposed parallel to the longitudinal axis of the prosthesis, disposed on the outside of the second prosthesis 3 and within the first prosthesis The exemplary embodiments disclosed in FIG. 13 may be used in combination with any of the other exemplary embodiments described herein. The embodiments described by FIG. 14 are desirable because this sensor arrangement preferably maximizes the stretching component of the signal relative to the "bulging" mechanical aspect of the fluid flow through the prosthesis. As an added benefit, given the small total volume of PVDF sensing material present in this sensor arrangement (e.g. element 35) it preferably has lower power requirements relative to other sensor arrangements.

FIG. 15 discloses an exemplary embodiment of the prosthesis disclosed in FIG. 1 wherein the first or the second tubular prosthesis has a longitudinal axis, and wherein the sensor is disposed transverse to the longitudinal axis. The sensor element 36 is disposed transverse in an open structure around element 3 and within element 2. The exemplary embodiments disclosed in FIG. 15 may be used in combination with any of the other exemplary embodiments described herein. The embodiments described by FIG. 15 are desirable because this sensor arrangement preferably allows for the prosthesis (or individual lumen) to expand fully without being constrained (like a closed annular band would do) while at the same time obtaining a good signal in the "bulging" direction. As an added benefit, this orientation preferably will make use of one or more non-closed loop bands at various angles to obtain better resolution for specific signals of interest (e.g. signals causing the graft to "bulge" or it to stretch longitudinally.

FIG. 16 discloses an exemplary embodiment of the prosthesis disclosed in FIG. 1 wherein the sensor comprises a plurality of undulating elongated elements disposed over the first and/or the second tubular prosthesis. In FIG. 16a the sensor element 37 is an undulating elongated element that forms a complete ring around the circumference of the prosthesis and is disposed around element 2. In FIG. 16b the sensor element 38 is an undulating elongated element that forms a complete ring around the circumference of the prosthesis and is disposed around 3 and within 2. In FIG. 16c, the sensor element 39 is an undulating elongated element that is disposed partially around 2. In FIG. 16d, the sensor element 40 is an undulating, elongated element that is disposed partially around 3 and is disposed entirely within 2. The embodiments described by FIG. 16 are desirable because this sensor arrangement preferably allows for the prosthesis (or individual lumen) to expand fully without being constrained (like a closed annular band would do) while at the same time obtaining an excellent signal in the stretching direction and a good signal in the "bulging" direction, especially at the harsh angle points on elements 37-40.

Figure 17A:
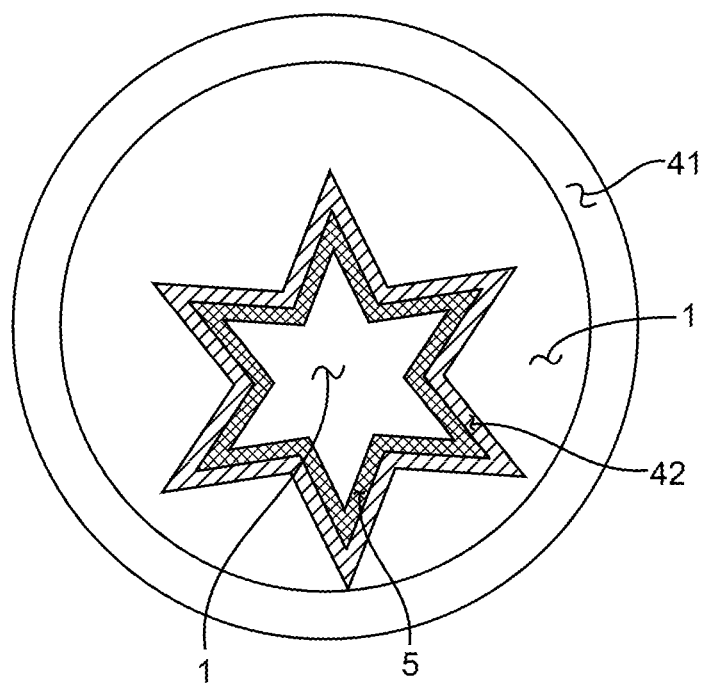
FIGS. 17A-17B show a prosthesis and sensor which has a collapsed configuration sized for delivery of the package, and an expanded configuration adapted to match the anatomy in which the sensor is deployed.
Figure 17B:
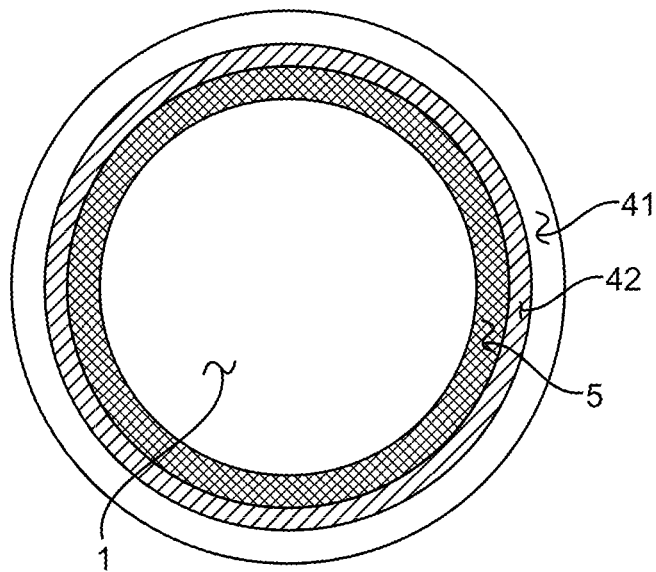

FIG. 17 discloses an exemplary embodiment of the prostheses disclosed in FIG. 16 wherein the sensor has a collapsed configuration sized for delivery of the sensor and an expanded configuration adapted to substantially match an anatomy in which the sensor is deployed, and wherein in the expanded configuration the sensor forms a closed annular band. In FIG. 17a the sensor 42 is collapsed and disposed over a collapsed stent 5 for delivery into a lumen 1 of a conduit 41. In FIG. 17b, 42 is in an expanded configuration that matches 1 and 41 due to the expansion of 5, and also forms a closed annular band disposed around 5. The exemplary embodiments disclosed in FIG. 17 may be used in combination with any of the other exemplary embodiments described herein. The embodiments described by FIG. 17 are desirable because this sensor arrangement preferably allows for the prosthesis (or lumen) to expand fully (from a starting point from which it is collapsed) while at the same time conforming to both the collapsed and expanded shapes. In addition, the sensor 42 while at the same time obtaining an excellent signal in the "bulging" direction. FIG. 18 discloses an exemplary embodiment of the prosthesis disclosed in FIG. 1 wherein the sensor is disposed circumferentially around the first or the second tubular prosthesis to form a closed annular band therearound. In FIGS. 18a and 18b the sensor element 43 is disposed around element 3 and within element 2 in a closed loop structure normal to the longitudinal axis of the prosthesis. In FIGS. 18c and 18d the sensor element 44 is disposed around element 2 in a closed loop structure normal to the longitudinal axis of the prosthesis.

The exemplary embodiments disclosed in FIG. 18 may be used in combination with any of the other exemplary embodiments described herein. The embodiments described by FIG. 18 are desirable because this sensor arrangement preferably allows for the prosthesis to get a very large signal in the "bulging" direction. This closed loop sensor 43 preferably will give the strongest signal in this "bulging" direction over any other sensor trying to obtain only a signal in this direction.

FIG. 19 discloses an exemplary embodiment of the prosthesis disclosed in FIG. 1 wherein the sensor is partially disposed circumferentially around the first or the second tubular prosthesis to form an open annular band therearound. In FIGS. 19a and 19b the sensor element 45 is disposed around element 3 and within element 2 in an open annular band normal to the longitudinal axis. In FIGS. 19c and 19d the sensor element 46 is disposed around element 2 in an open annular band normal to the longitudinal axis. The embodiments described by FIG. 19 are desirable because this sensor arrangement preferably allows for the prosthesis (or individual lumen) to expand fully without being constrained (like a closed annular band would do) while at the same time obtaining a good signal in the "bulging" direction. As an added benefit, if the sensor is oriented normal to the longitudinal axis, it will preferably give a high quality signal in the "bulging" direction while not sacrificing significant signal intensity.

Protection of the sensor element and any components related to data processing and transmission can be desirable in certain circumstances, for example 1) a bodily response to the sensor could harm the animal; and 2) a bodily response could affect the basic functioning of the device. Therefore, it is preferred that the sensor and any components related to data processing and transmission be protected as much as possible from exposure to the body's immune response. To this end, any of the embodiments mentioned herein may benefit from optional additional protective layers being attached to the sensor and the data processing/transmission components. Given the various configurations that are possible for the device, a flexible or conformable protective is preferred to encapsulate these components. Possible materials for this include, but are not limited to silicone, polydimethylsiloxane, polyvinylalcohol, parylene, polyester, PTFE, ePTFE, polyethylene terepthalate, or other suitable polymer, metal, and/or metal oxide thin film coatings.

As described herein, there is a significant need for monitoring tubular prostheses that are used to carry bodily fluids in a subject such as a human patient or a veterinary patient. For example, for patients with blocked blood flow in their peripheral arteries, synthetic vascular grafts are frequently used to bypass these blockages. These implantable grafts are intended to last in patients for up to five years, however there is a very high rate of failure of these devices within the first year of implantation. Typically, when a graft fails, it becomes blocked and eventually stops functioning as a blood carrying entity. When a graft reaches complete blockage it is unsalvageable and must be replaced, or even worse, the patient must go through an amputation of the part of the body to which the graft was responsible for supplying blood. Interestingly enough, grafts can be salvaged if they are not completely blocked. In fact, even a graft that is 95% blocked can be salvaged using a reopening procedure such as an angioplasty. After reopening, the vast majority of vascular grafts are able to survive for their intended duration in the patient. Since the vast majority of these blockages typically form gradually over time (non-acutely), it would be possible to entirely avoid these catastrophic and costly outcomes if a system was developed such that the health of the graft could be monitored regularly by a clinician. Existing approaches for solving this problem have a number of challenges. Currently, patients are tested 1-2 times per year with duplex ultrasound, a dedicated imaging machine that can only be used in hospitals. Furthermore, duplex ultrasound requires a highly trained technician and/or clinician to interpret the health of the graft. Because duplex ultrasound is the only technology available to clinicians today, testing can only occur in hospitals, requires a separately scheduled appointment, is very costly, and produces results that are very difficult to interpret. The gold-standard metric for assessing graft health today is measurement of peak flow velocity of the blood flow through a graft. This is then correlated to occlusion percentages to make a determination of what course of action to take with a patient. While this test is accurate when carried out by skilled clinicians, unfortunately, it is carried out too infrequently. Blockages often form in a matter of weeks, so a frequency of testing once every six months can be inadequate. Therefore, it would be beneficial to develop a system whereby graft health can be assessed at regular intervals from a convenient location such as a patient's home. Preferably, this system would enable remote assessment and monitoring of the patient's graft health such that a sensor disposed with the graft in the patient would be able to eventually transmit data directly to a clinician, electronic medical record, hospital, or other care provider. This would allow clinicians to interpret this data and then decide whether a further diagnostic study or other intervention such as an angioplasty would be needed.

In another aspect, system for monitoring fluid flow through one or more hollow conduits such as allograft vessels, xenograft vessels or tubular prostheses such as grafts, stent-grafts or stents made from materials such as ePTFE, PTFE, polyester, polyethylene terephthalate, nitinol, cobalt chromium alloy, stainless steel, bioabsorable polymers such as PGA, PLA, etc., or another suitable flexible and/or expandable substrate used as a tubular prosthetic in the body is disclosed. This aspect of the invention or any exemplary embodiments of this aspect of the invention may include one or several of the exemplary embodiments described herein relating to any other features of the embodiments disclosed herein and may comprise a prosthetic with a lumen extending therethrough with the lumen configured for fluid flow therethrough and a sensor operatively coupled with the prosthesis and configured such that it can sense fluid flow and output data related to patient health, fluid flow, flow rate, flow velocity, wall thickness, stenosis, non-laminar flow, turbulent flow, occlusion, occlusion percentage, or occlusion location. In an exemplary embodiment, the system may also incorporate a wireless transmitter such that data can be transmitted from the sensor to another location. This location could be a remote location, or any location that is located intracorporeally or extracorporeally. In another exemplary embodiment a display device is operative coupled with the sensor and is configured to display the output data. In this exemplary embodiment, the display device may be operatively coupled remotely or directly with the sensor. For example, if sensor output is transmitted to one or more external devices and eventually to a clinician's mobile device or computer, the display of the mobile device would be considered to be operatively coupled with the sensor. A number of display devices are possible for this including mobile phones, tablets, personal computers, televisions, instrument displays, watches, optical head-mounted displays, wearable electronics, augmented reality devices such as contact lenses, glasses or otherwise. In another exemplary embodiment a processor is operatively coupled with the sensor and configured to process the output data. As with the operatively coupled display in the prior exemplary embodiment, the processor may be operatively coupled remotely or directly to the sensor. For example, if sensor output was transmitted to one or more external devices and eventually to a processor which is configured to process the output data, the processor would be operatively coupled with the sensor.

Several processors are known to those skilled in the art and an appropriate processor may be selected from the known art for any of the embodiments disclosed herein. In another exemplary embodiment the system further comprises an operatively coupled power source for providing power to the system. As mentioned earlier, operative coupling may be direct or remote. For example the power source could be a battery which is either implanted in the patient or resides outside of the body. Another example of a power source is an RF source which through inductive coupling is able to supply power to the implanted components of the system. The benefit of an RF inductively coupled power supply is that it eliminates the need for an implantable or otherwise directly connected battery. In another exemplary embodiment, the system comprises a low power sensor which is essentially passive and does not require power supplied thereto to sense fluid flow. In another exemplary embodiment the system comprises a lower power sensor and transmitter which are both essentially passive and do not require power supplied thereto to sense fluid flow and output data related to fluid flow.

Figure 20:
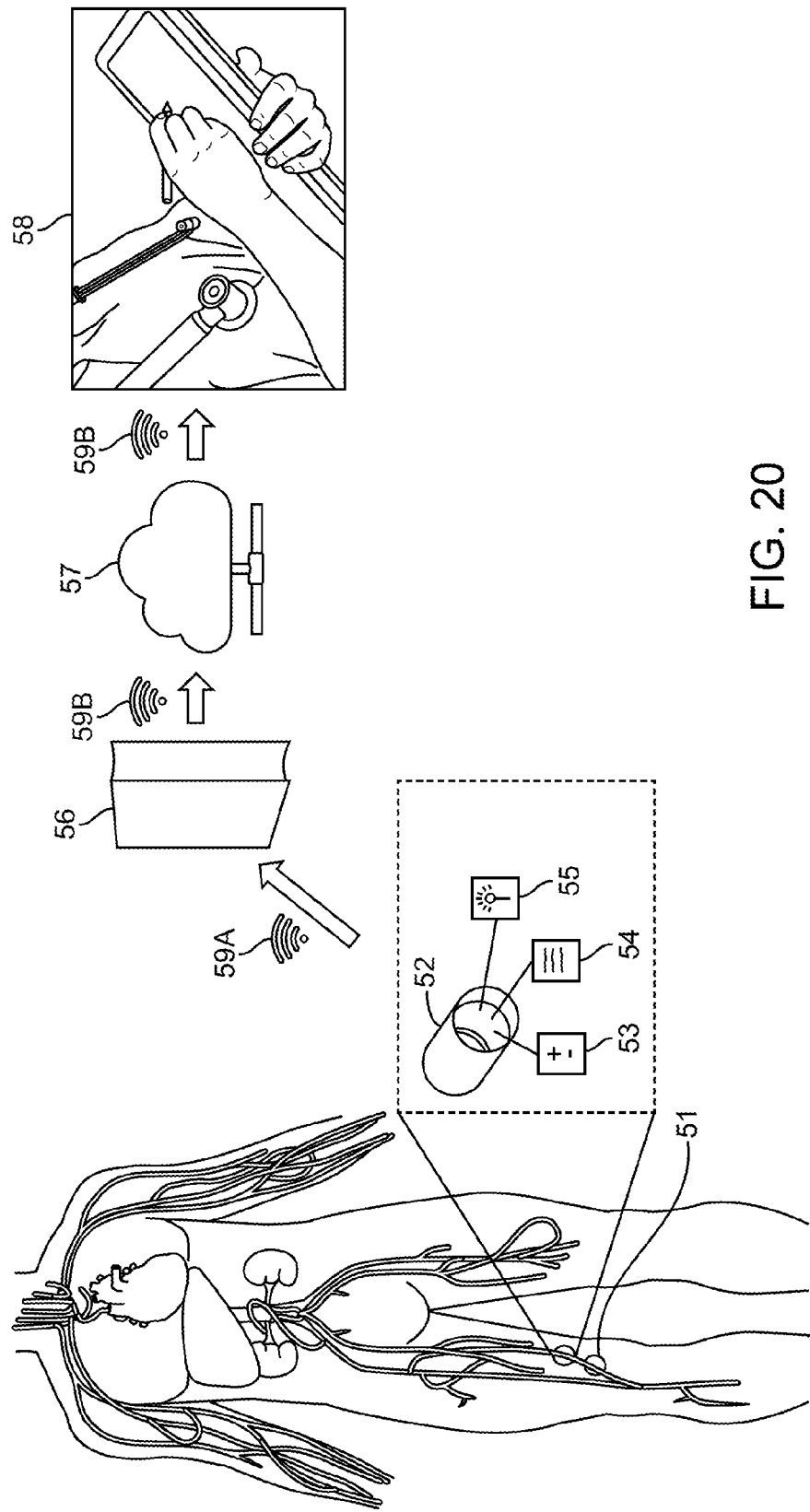
FIG. 20 shows a system where a tubular prosthesis is monitored by a sensor and the data is then processed and transmitted to a medical practitioner for review.

The benefit of such a sensor and/or transmitter is that it minimizes the power needed to support the system. This is a desirable feature for the system since a low power footprint enables the use of a smaller battery and also makes RF inductively coupled power more practical for application in the system. In another exemplary embodiment an integrated circuit chip is operatively coupled with the sensor. As mentioned earlier, operative coupling may be direct or remote. The integrated circuit may contain a data transmitter and/or processor. The benefit of using an integrated circuit is that it offers the capability of a data transmitter, data processor, and/or processor/transmitter. In another exemplary embodiment the system further comprises a data transmitter either as part of an integrated circuit chip or as a standalone transmitter that is operatively coupled with the sensor and transmits using one or several of the following communication methods: radiofrequency (RF), Bluetooth, WiFi, or other near-field communication means. Another exemplary embodiment further comprises a receiver for receiving sensor data from the sensor. The receiver may be disposed intracorporeally or extracorporeally. The receiver could process the sensor data and then transmit data to a display device which is configured to display the data to a physician or other caregiver. As mentioned earlier any of the features described in exemplary embodiments disclosed herein may be used in combination with or substituted with one or several other features disclosed in any of the other exemplary embodiments disclosed herein. FIG. 20 discloses an exemplary embodiment of a system for monitoring flow through a prosthesis, the system comprising: a prosthesis having a lumen extending therethrough, the lumen configured for fluid flow therethrough; and a sensor operatively coupled with the prosthesis, the sensor configured to sense a characteristic of the fluid flow and output data related to the fluid flow. In FIG. 20, any of the exemplary embodiments of prostheses mentioned herein 52 are implanted into a hollow conduit 51 in the body to preferably improve flow through 51. Element 52 optionally may be coupled with an integrated circuit 54, a power source 53 and/or a transmitter 55. The sensor data is transmitted wirelessly 59a to an external receiver 56. Element 56 contains a processor to process the raw data into a signal that is transmitted wirelessly 59b optionally to an external site for storage 57 and ultimately to a display monitor or device 58 which can be read by a clinician or other care provider.

In another aspect of the present invention, a method for monitoring flow through a hollow conduit such as a prosthesis is disclosed. Any of the exemplary embodiments of this aspect of the invention may use one or several of the exemplary embodiments of the fluid monitoring prosthesis disclosed herein. This method may comprise providing a prosthesis having a lumen therethrough and a sensor coupled to the prosthesis; coupling the prosthesis to a fluid path in a patient so that fluid flows through the prosthesis; sensing the fluid flow with a sensor transmitting data representative of the sensed fluid flow to a receiver disposed extracorporeally relative to the patient and outputting the data. In an exemplary embodiment the prosthesis is a prosthetic vascular graft such as one made from a material like PTFE, ePTFE, polyester, polyethylene terephthalate, nitinol, colbalt chromium alloy, stainless steel, bioabsorbable polymers such as PGA, PLA, etc., or another suitable flexible and/or expandable material. The prosthetic vascular graft may be a graft, stent, or stent-graft. The fluid path also may be comprised of a blood flow path, urinary flow path, cerebrospinal flow path, lymph flow path, or flow path of another bodily fluid. Transmitting the data may comprise sending the data wirelessly to another device or system which is operatively coupled to the sensor.

Figure 24:
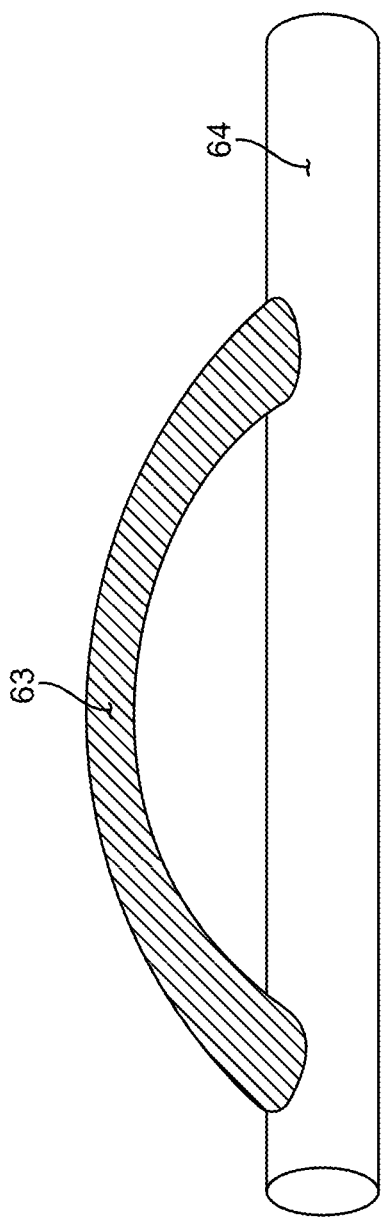
FIG. 24 shows a prosthesis which is attached by end-to-side anastomoses.
Figure 28:
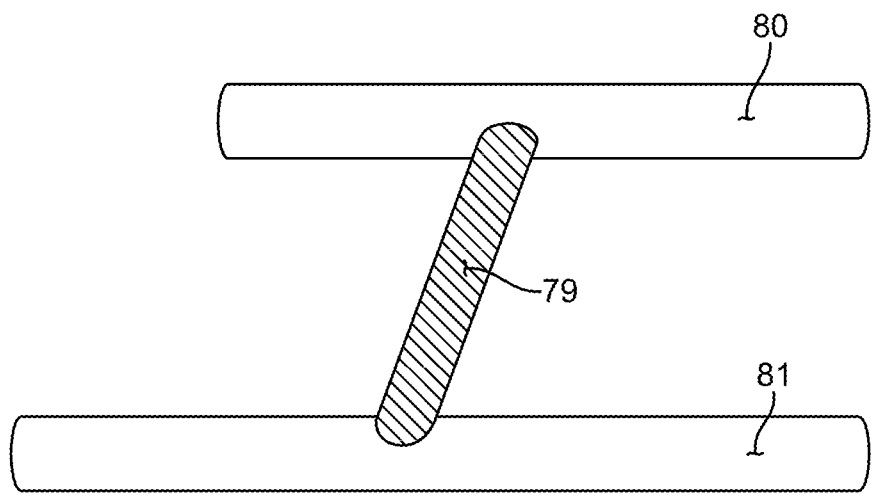
FIG. 28 shows a prosthesis which is attached by end-to-side anastomoses between two distinct vessels, such as a fistula.

The tubular prosthesis described above is used in an anastomosis procedure to replace or bypass a section of damaged or stenotic blood vessel, as is known to those skilled in the art. The procedure of implanting a tubular prosthesis in order to bypass a lesion in a single vessel (FIG. 24), the original vessel being depicted by 64 and the prosthesis by 63, and the orifices of the tubular prosthesis being attached by end-to-side anastomoses. In FIG. 28, the utilization of a tubular prosthesis 79 to connect two distinct vessels (elements 80 and 81) is described. In order to implant the tubular prosthesis, a healthy section of blood vessel is selected adjacent to the damaged blood vessel. The vessel is appropriately accessed and an aperture is formed in the healthy section of distal blood vessel. The aperture is formed to appropriately accommodate the distal orifice of the tubular prosthesis. The distal end of the tubular prosthesis is then joined appropriately by the medical practitioner to the aperture such as by suturing the ends together, stapling or gluing them together. A subcutaneous conduit or tunnel is then created in the adjacent tissue in order to accommodate the body of the tubular prosthesis. The step of forming an aperture is repeated in a second section of healthy blood vessel at the proximal end of the damaged section of blood vessel or the aperture may be created in an altogether different blood vessel. Once again, an appropriately sized shaped aperture is created to accommodate the proximal end of the tubular prosthesis. The proximal end of the tubular prosthesis is then joined to this aperture using similar techniques as previously described. During the implantation procedure, blood is typically prevented from passing through the blood vessel being operated on; but, once the proximal and distal ends are appropriately attached, blood is allowed to pass through the blood vessel and into the tubular prosthesis.

In another exemplary embodiment, the method whereby the tubular prosthesis may be used in a procedure where a venous cuff is employed by one skilled in the art is described. In this method, depicted in FIG. 23, the distal orifice of the tubular prosthesis 60 is attached to the proximal orifice of an autograft or allograft 61, such as a saphenous or antecubital vein. The distal orifice of the autograft is then attached to the aperture created in the relevant vessel 62. The proximal orifice of the tubular prosthesis is attached to the vessel providing fluid inflow. The distal anastomotic site is a known area of increased intimal hyperplasia and possible stenosis. Utilizing a venous cuff has been shown to reduce the amount of intimal hyperplasia formation and stenosis formation, as described by Neville, et al. Eur J Vasc Endovasc Surg. August 2012. It may prove advantageous to utilize this method to not only reduce the likelihood of stenosis formation, but to also enable monitoring of the prosthetic. In another embodiment, the tubular prosthesis may also be attached to another synthetic or stem-cell derived graft, as needed.

In the reverse of the embodiment above, a method whereby an autograft or other synthetic is utilized as the main body of the bypass, repair or replacement by one skilled in the art is described. In this method, the distal orifice of the autograft or other synthetic graft such as ePTFE, or polyester grafts like Dacron, is attached to the proximal orifice of the tubular prosthesis. The distal orifice of the tubular prosthesis is then attached via methods known by those skilled in the art to an aperture created in the relevant vessel. The proximal orifice of the autograft, allograft, xenograft or other synthetic or stem-cell derived graft is attached to the vessel providing fluid inflow. This method allows for a minimization of immune response while allowing the tubular prosthesis to report data relating to the aforementioned parameters.

Figure 25:
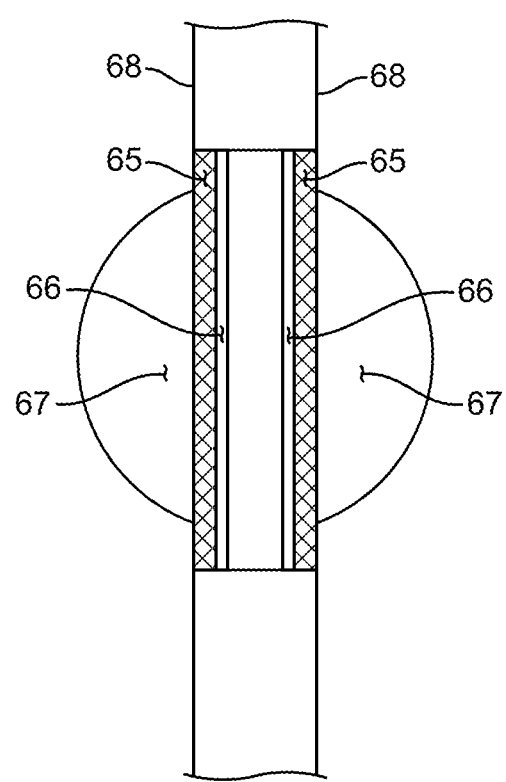
FIG. 25 shows a prosthesis, such as a stent graft, which is used to bridge an aneurysmal sac.

Transluminal stent-graft placement and other methods of device delivery are well-known to those skilled in the art (see U.S. Pat. Nos. 7,686,842, 8,034,096). Open surgical placement of a stent-graft device is also defined in U.S. Pat. No. 8,202,311. A method whereby a tubular prosthesis comprising a stent-graft, as described above, is capable of being deployed in a similar manner by those skilled in the art will be briefly described, and is depicted in FIG. 25. In FIG. 25 the vessel which has an aneurysm is depicted by element 68 and the aneurysmal sac is depicted by element 67. The stent portion of the stent graft is depicted by element 65 and the graft portion by element 66. A sheath is introduced into an appropriate vessel using known techniques such as a surgical cutdown or a percutaneous procedure like the Seldinger technique, and then advanced to the appropriate position, preferably over a guidewire. In the case of an aneurysm or rupture, an occlusion balloon catheter may be advanced and deployed in order to control bleeding. Imaging modalities may be used to size the required tubular prosthesis; this may also be accomplished via a calibration guidewire. Once appropriately sized, the tubular prosthesis is loaded onto the distal tip of a sheath or catheter and delivered to the appropriate surgical site. In a preferred embodiment, the tubular prosthesis is mounted over a delivery catheter which is then delivered to the target treatment site, preferably over a guidewire. An imaging modality may then be utilized to ensure correct placement before deployment. The tubular prosthesis may include a self-expanding stent which deploys upon retraction of a constraining sheath therefrom, or the tubular prosthesis may include a balloon expandable stent which is deployed by a balloon or other expandable member on the delivery catheter. Full expansion of the stent-graft is assured by optional dilation with the aid of an expandable member such as a balloon on the delivery catheter or another catheter which also tacks the stent-graft into position. An imaging modality is once again utilized to ensure stent-graft patency without evidence of migration, vessel rupture, perigraft leak, or dissection.

In another embodiment, the method of deployment may involve a stent or stent-graft which is capable of self-expansion or self-deployment via an electrical current being induced across the sensor which may be a piezoresistive element. For example, the piezoresistive element may generate a current which passes through the stent portion of the stent or stent-graft, resulting in heating of the stent thereby elevating the stent temperature above a transition temperature which results in self-expansion of the stent. Shape memory alloys such as nickel titanium alloys are well known in the art and can be used in this embodiment. The piezoresistive element is capable of sensing pressure, among other previously identified characteristics, and then transmitting this data via a transmitter operatively coupled to the prosthesis to the medical practitioner and being preset for a particular amount of stress, this embodiment would aid in the possible prevention of leaks, ruptures or dissections, or overexpansion of the stent-graft. In another method, an appropriate imaging modality may be utilized to ascertain the size of the relevant lumen. The piezoresistive element may then be programmed or preset to demonstrate a particular amount of strain or stress. The medical practitioner may then induce an appropriate electrical current via mechanisms known by those skilled in the art into the piezoresistive element. This would allow the piezoresistive element to aid in maintaining the patency of the lumen and may help prevent leaks, ruptures, dissections, overexpansion, etc.

Figure 26A:
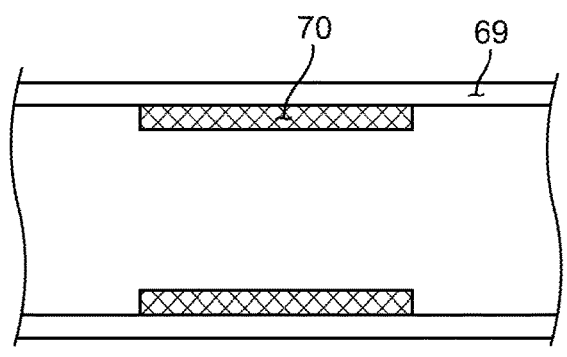
FIGS. 26A-26B show a prosthesis.
Figure 26B:
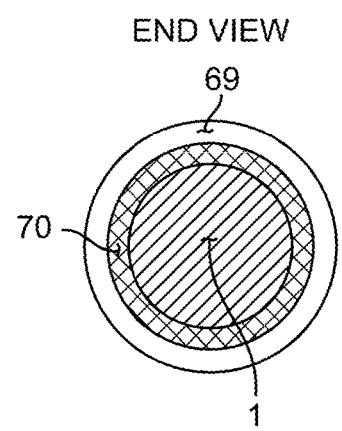
Figure 27D:
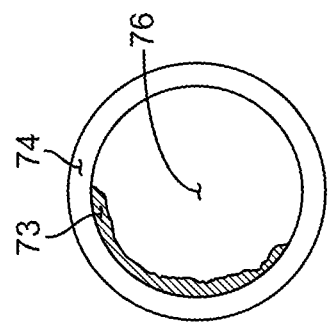
FIGS. 27A-27D shows a prosthesis wherein an expandable member or other intervention is utilized to increase patency within the lumen.
Figure 27C:
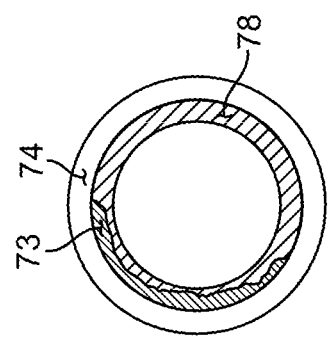
Figure 27B:
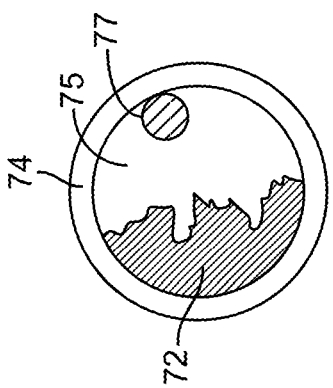
Figure 27A:
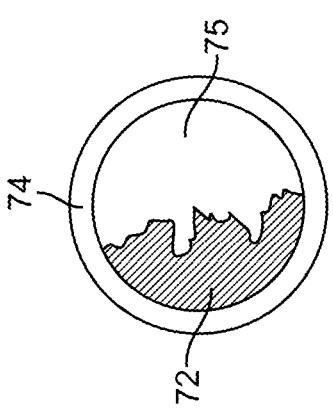

A method of deploying a tubular prosthesis in the form of a stent, as defined by those skilled in the art and partially described by U.S. Pat. Nos. 8,551,156, 8,597,343, 8,579, 958, etc., in order to monitor parameters regarding flow or occlusion is described. FIG. 26 depicts a stent 70 which has been placed in a vessel 69. A stent may be used to maintain patency of any hollow conduit within the body. Stents are typically positioned within the appropriate vessel or conduit and then expanded from within using a stent delivery balloon and/or an angioplasty balloon, as is known to those skilled in the art, or the stent may be a self-expanding stent which expands when a constraint is removed, or when the stent is heated above a transition temperature. A sensor may be coupled to the stent to monitor flow through the stent.

In another embodiment, one orifice of the tubular prosthesis is placed transluminally into a vessel, the other orifice is then attached to either or the same vessel or another vessel via an end-to-end or end-to-side anastomosis. This utilization of a hybrid stent graft is well known to one skilled in the art and is described by Tsagakis K et al. Ann Cardiothorac Surg, September 2013.

The tubular prosthesis described above may also be used in an anastomosis procedure to replace or bypass a section of damaged or stenotic ureteral vessel, as known to those skilled in the art. A method of implanting a tubular prosthesis in order to bypass a lesion in a single vessel or to connect two distinct vessels to enhance the drainage of urine is described. In order to implant the tubular prosthesis, a healthy section of ureteral vessel is selected adjacent to the damaged vessel. The vessel is appropriately accessed and an aperture is formed in the healthy section of distal ureter. The aperture is formed to appropriately accommodate the distal orifice of the tubular prosthesis. The distal end of the tubular prosthesis is then joined appropriately by the medical practitioner to the aperture using methods known in the art such as by suturing, stapling, gluing, etc. A conduit or tunnel is then created in the adjacent tissue to accommodate and secure the body of the tubular prosthesis. The step of forming an aperture is repeated in a second section of healthy ureter at the proximal end of the damaged section of ureter or the aperture may be created in an altogether different hollow conduit, such as the contralateral ureter, bladder, urethra, colon or external container with a transcutaneous conduit. Once again, an appropriately sized and shaped aperture is created to accommodate the proximal end of the tubular prosthesis. The proximal end of the tubular prosthesis is then joined to this aperture similarly as the distal end. During the implantation procedure, urine is typically prevented from passing through the ureter being operated on; but, once the proximal and distal ends are appropriately attached, urine is allowed to pass through the blood vessel and into the tubular prosthesis. An imaging modality will be used to ensure flow through the tubular prosthesis and lack of leaks, ruptures, dissections, etc.

In another embodiment, the tubular prosthesis described above may be used as a ureteral stent, designed to be placed within a patient's ureter to facilitate drainage from the patient's kidneys to the bladder, as described in U.S. Pat. No. 6,764,519. The method includes placement of a ureteral stent device in a ureter of a patient, as is known to those skilled in the art.

In yet another embodiment, the tubular prosthesis described above may be used as a urethral stent (such as U.S. Pat. No. 5,681,274) designed to be placed within a patient's urethra to facilitate drainage from or through the patient's kidney or bladder to the external environment. The method of deployment for a urethral stent is well known to those skilled in the art. In another embodiment, this stent may be biodegradable in such a fashion that flow may be monitored temporarily. As the stent biodegrades, the sensor would be expelled via the flow of urine.

In another embodiment, a tubular prosthesis as described above may be used as a urinary catheter, as described in U.S. Pat. No. 4,575,371. In this method, the urinary catheter is designed to be placed within an orifice residing within the bladder of an individual, as is known to those skilled in the art. The tubular prosthesis would then act as a urinary catheter to facilitate drainage of urine from or through the patient's bladder to an extracorporeal container.

An embodiment whereby the tubular prosthesis is utilized as a transjugular intrahepatic portosystemic shunt (TIPS); a method and device being described in U.S. Pat. No. 8,628,491. The method described here is useful for monitoring flow and/or occlusion parameters in a synthetic shunt between the portal vein from a hepatic vein. The creation of a transjugular intrahepatic portosystemic shunt is well known to those skilled in the art and allows blood to bypass the hepatic parenchyma responsible for elevated portal vein pressures and is described here. After being sufficiently anesthetized, the patient's right internal jugular vein is accessed and a catheter is advanced via the superior vena cava, the right atrium, and inferior vena cava to the right hepatic vein. A sheath is then guided into the right hepatic vein. A large needle is then pushed through the wall of the hepatic vein into the parenchyma anteroinferomedially in the expected direction of the right portal vein. When blood has been aspirated, an imaging modality is utilized to ensure access into the right portal vein. A guidewire is then advanced into the main portal vein. An expandable member is placed over this wire and dilated creating a conduit between the hepatic system and the portal system. A tubular prosthesis as described above, is then placed within the conduit and dilated forming the intrahepatic portosystemic shunt. If the patient is not suitable for a transluminal delivery of the shunt, an open surgery may be performed by a surgeon, interventional radiologist or other trained medical professional. In this embodiment, apertures are created between both the right, left or common hepatic vein and the portal vein. A shunt is then created by attaching each orifice of the tubular prosthesis described above to its relevant aperture. Expansion of the stents in the stent-graft anchor the prosthesis in the desired position.

Another embodiment is a method whereby flow and/or occlusion parameters, pursuant to a liver resection or transplant by those skilled in the art, are monitored within the portal and hepatic systems via any of the tubular prostheses described above.

Another embodiment is a method whereby any of the tubular prostheses described above is employed as a cerebrospinal fluid shunt system for the monitoring and treatment of hydrocephalus. The creation of a cerebrospinal fluid shunt system is well known to those skilled in the art.

In another embodiment, any of the tubular prostheses disclosed herein is employed as a drainage apparatus for cerebrospinal fluid (which may contain blood) and is utilized as a method for the monitoring and treatment of cerebral or spinal damage. In this method, the tubular prosthesis is to be implanted by one skilled in the art with an orifice located at the site which is to be drained. The prosthesis may be interrogated either continuously and/or at a series of predefined time points and/or on an ad hoc basis.

Another embodiment is a method whereby any of the tubular prostheses described herein is employed as a drainage apparatus during a surgical procedure. In this method, the prosthesis may be interrogated by one skilled in the art for data either continuously and/or at a series of predetermined time points and/or on an ad hoc basis.

Yet another embodiment is a method whereby any of the tubular prostheses is employed as a drainage apparatus post-surgical procedure. In this method, the tubular prosthesis is appropriately secured by one skilled in the art. The prosthesis may then be interrogated by one skilled in the art for data either continuously and/or at a series of predetermined time points and/or on an ad hoc basis.

Figure 29:
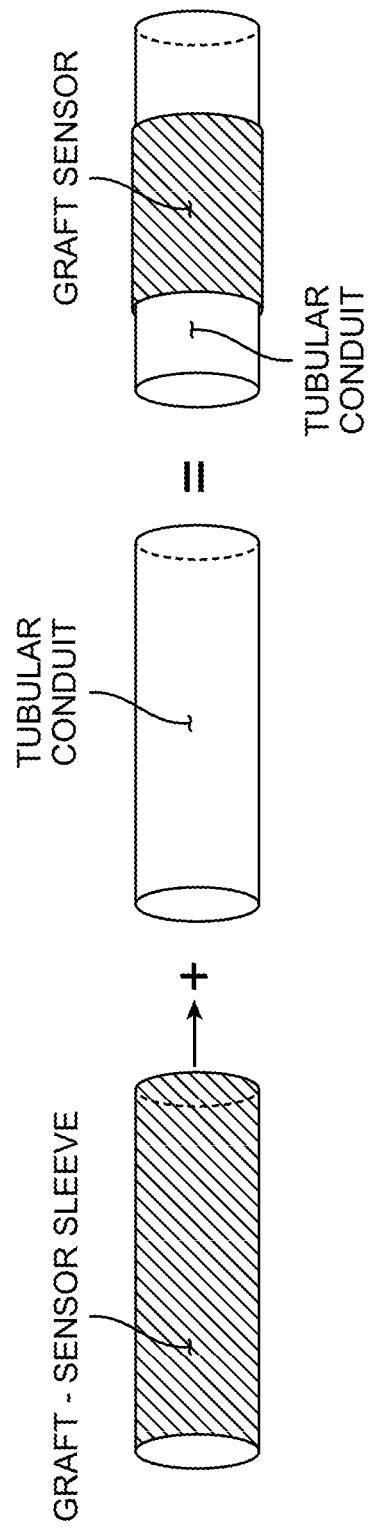
FIG. 29 shows a prosthesis which is slidably engaged over the top of another tubular conduit.
Figure 30:
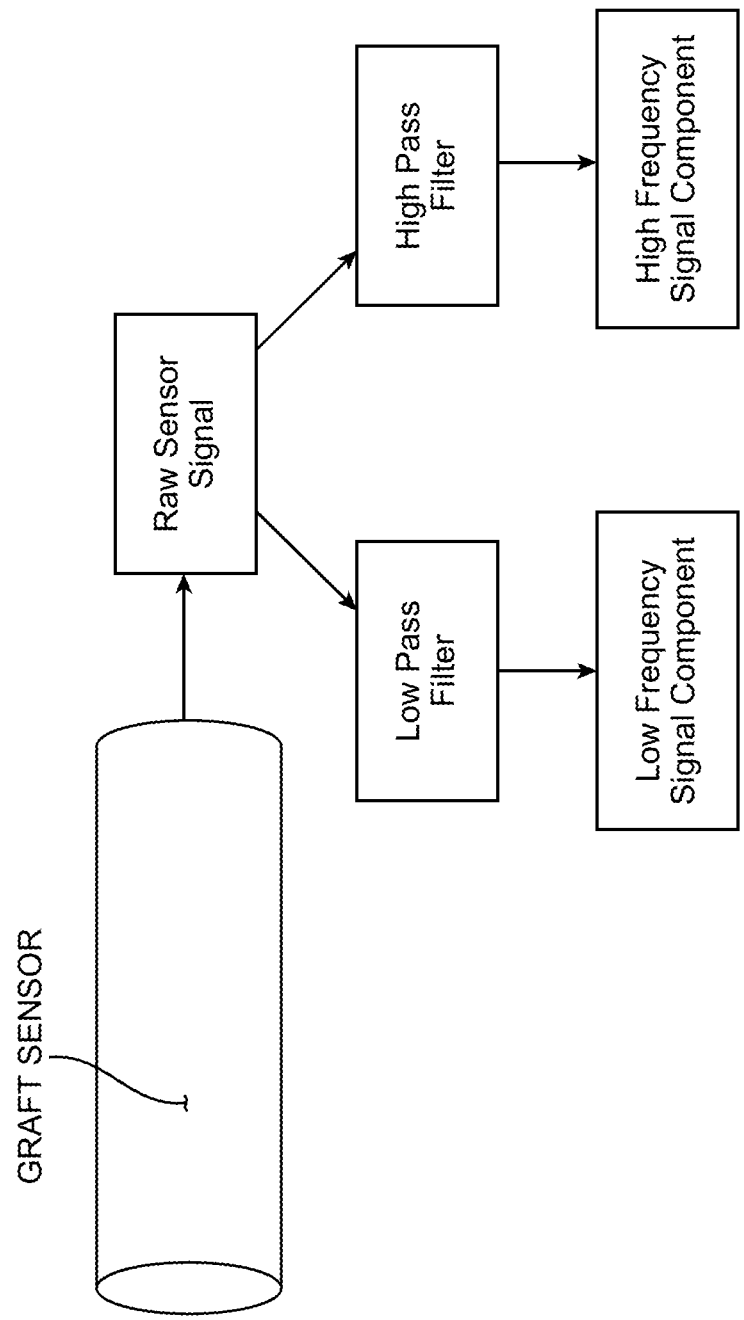
FIG. 30 shows characteristics of a signal representing the fluid flow.

FIG. 29 discloses another exemplary embodiment wherein a method of coupling comprises slidably engaging the prosthesis over a native vessel or another prosthesis. In this method the tubular prosthesis is slid over the vessel to be monitored. This vessel may be any natural hollow conduit within the body or may be any autograft, allograft, xenograft, stem-cell derived or synthetic conduit which is being placed within the body and may need to be monitored.

A method whereby the tubular prosthesis is monitored after the implantation procedures described above is described herein. After placement of the tubular prosthesis, correct placement may be assured via an imaging modality such as ultrasound or angiography or by allowing fluid to pass through the lumen. Prior to data acquisition the sensor is preferably activated and paired with an enabled device. Data requisitioned from the tubular prosthesis by the medical practitioner can then be reviewed. In a preferred embodiment, upon review of the sensed data, the medical practitioner can determine whether flow through the prosthesis is adequate. If the medical practitioner were to deem the flow adequate, he or she may continue to interrogate the device at predetermined time intervals or shorten the time interval based on clinical judgment. If the medical practitioner were to deem the flow inadequate, he or she may perform one of several procedures; such as a dilatation of the lesion and its surroundings with an expandable member such as a balloon angioplasty catheter, administration of a lytic agent, removal and replacement of the prosthesis or a procedure whereby the lesion is broken up and the resultant debris removed from the lumen, such as an embolectomy. These methods are depicted in FIG. 27, wherein element 72 is the lesion as it may appear prior to intervention and element 73 is the lesion post-intervention. In FIG. 27, the vessel is depicted by element 74 and the lumen by element 75. The expandable member is depicted in its closed configuration by element 77 and in its expanded configuration by element 78. In another embodiment, after review of the data, the medical practitioner may deem it necessary to conduct additional diagnostic testing, such as an ultrasound, Doppler ultrasound, computer aided tomography scan (CAT), magnetic resonance imaging (MRI), etc. Following a review of this data, the medical practitioner may choose to perform one of the procedures indicated above. In another embodiment, review of sensed data may take on a unique form. Data requisitioned from the sensor may be listened to as an audio file; this is enabled by current data acquisition methods which can produce a waveform audio format file (.wav file). The medical practitioner may choose to listen to the flow within the lumen and determine whether flow is adequate or an intervention may be necessary. In exemplary embodiments where the sensor includes a piezoresistive element, the piezoresistive element acts as a microphone picking up acoustic signals from within the lumen of the tubular prosthesis. This can help the medical practitioner identify turbulence or stenosis. In addition, this method is not encumbered by signal interference as may be encountered when utilizing a stethoscope or ultrasound to acquire acoustic signals from the lumen of a prosthesis.

As discussed above, in tubular prostheses occlusions can form anywhere across the length of a prosthetic. The consequences of stenosis (sometimes also referred to herein as occlusion) in a tubular prosthetic are devastating especially when the prosthetic is a blood-carrying conduit such as a synthetic vascular graft, stent, covered stent or stent-graft. Early detection can significantly improve outcomes of patients with stenosed prosthetics. The embodiments described herein preferably relate to detection of flow and/or stenosis in a tubular prosthetic.

In some embodiments, it may be desirable to integrate an acoustic sensor with a tubular prosthetic so that a surveillance system may be implemented to perform early detection of occlusion formation. Acoustic sensors are able to detect turbulent flow that is generated at the site of stenosis and determine the inner vessel diameter based upon the level of turbulence. In order for acoustic sensors to be effective, they must be close enough to the site of an occlusion/stenosis to detect acoustic signatures indicative of turbulent flow. The present inventors have conducted experimental studies for both synthetic vascular grafts and stents which suggest that there are critical distances beyond which a sensor will no longer be able to identify a stenosis. Additionally, traditional acoustic sensors such as a stethoscope have been used to detect occlusions by positioning the acoustic sensor distal of the occlusion. This is believed to be due to the limitations of the sensors placed outside of the body to detect the turbulent flow. The noises generated by the turbulent flow are generally higher in magnitude distal of the occlusion and therefore they can be detected by the extracorporeal acoustic sensor. However, when the acoustic sensor is positioned proximal of the occlusion, the sensor is unable to accurately sense the noises from the turbulent flow. Embodiments described herein are now able to overcome these challenges and thus an in vivo sensor is able to detect occlusions when positioned either proximal or distal of the occlusion.

In our experimental setup a graft and a covered stent were implanted into a human tissue phantom with acoustic sensors wrapped around the outside of the tubular prostheses. A pulsatile flow pump was operated at 60 beats per minute (BPM) at a 500 cc/min volumetric flow rate to mimic fluid flow through a peripheral artery. Synthetic occlusions of fixed diameter were inserted at various lengths in the graft and covered stent in order to determine the effective distance at which an occlusion could be detected by the acoustic sensor. It was determined that the effective distance at which a sensor could detect occlusion was also dependent upon the location of the occlusion relative to the sensor. If the occlusion occurred proximally to the sensor, the sensor could detect the occlusion if it was between 0 and 15 cm proximal to the sensor. If the occlusion was distal to the sensor, the sensor could detect the occlusion if it was between 0 and 3 cm distal to the sensor.

In bypass grafts, where occlusions form preferentially at anastomotic sites (approximately 60% form at a distal anastomotic site, approximately 35% form at a proximal anastomotic site), this discovery is very relevant since this informs a precise placement of sensors that may guarantee detection of virtually all occlusions. Our experiments show that an occlusion that is no more than 3 cm away from the distal anastomotic site and no more than 15 cm away from the proximal anastomotic site will be able to detect virtually all occlusions in the graft.

In all tubular prosthetics this experimental data also informs the precise distribution of sensors that ensures any occlusion formed along the length of prosthetic will be detectable by an acoustic sensor on the prosthetic. The number of sensors will be dependent upon the length of the prosthetic. Keep in mind, at a minimum, there preferably is at least one sensor that is within 3 cm of the distal end of the prosthetic, and at least one sensor which is within 15 cm of the proximal end of the prosthetic. If the prosthetic is less than or equal to 18 cm in length, one sensor will be sufficient for detecting an occlusion anywhere along the length of the prosthetic. If the prosthetic is more than 18 cm in length, but less than or equal to 36 cm in length, two sensors may be desirable to meet this constraint (one sensor that is 3 cm from the distal end of the prosthetic, and one sensor that is 15 cm away from the proximal end of the prosthetic). If the prosthetic is greater than 36 cm in length but less than or equal to 54 cm in length, then 3 acoustic sensors may be desirable. In prosthetics of these lengths, the following approach should yield a desirable arrangement of sensors to ensure detection along the entire length of the prosthetic. One sensor could be placed 3 cm from the distal end of the prosthetic, and a second sensor placed 15 cm from the proximal end of the prosthetic. The third sensor can be placed anywhere between the distal and proximal sensors, but should be no more than 18 cm upstream of the sensor closest to the distal end of the prosthetic.

Figure 31:
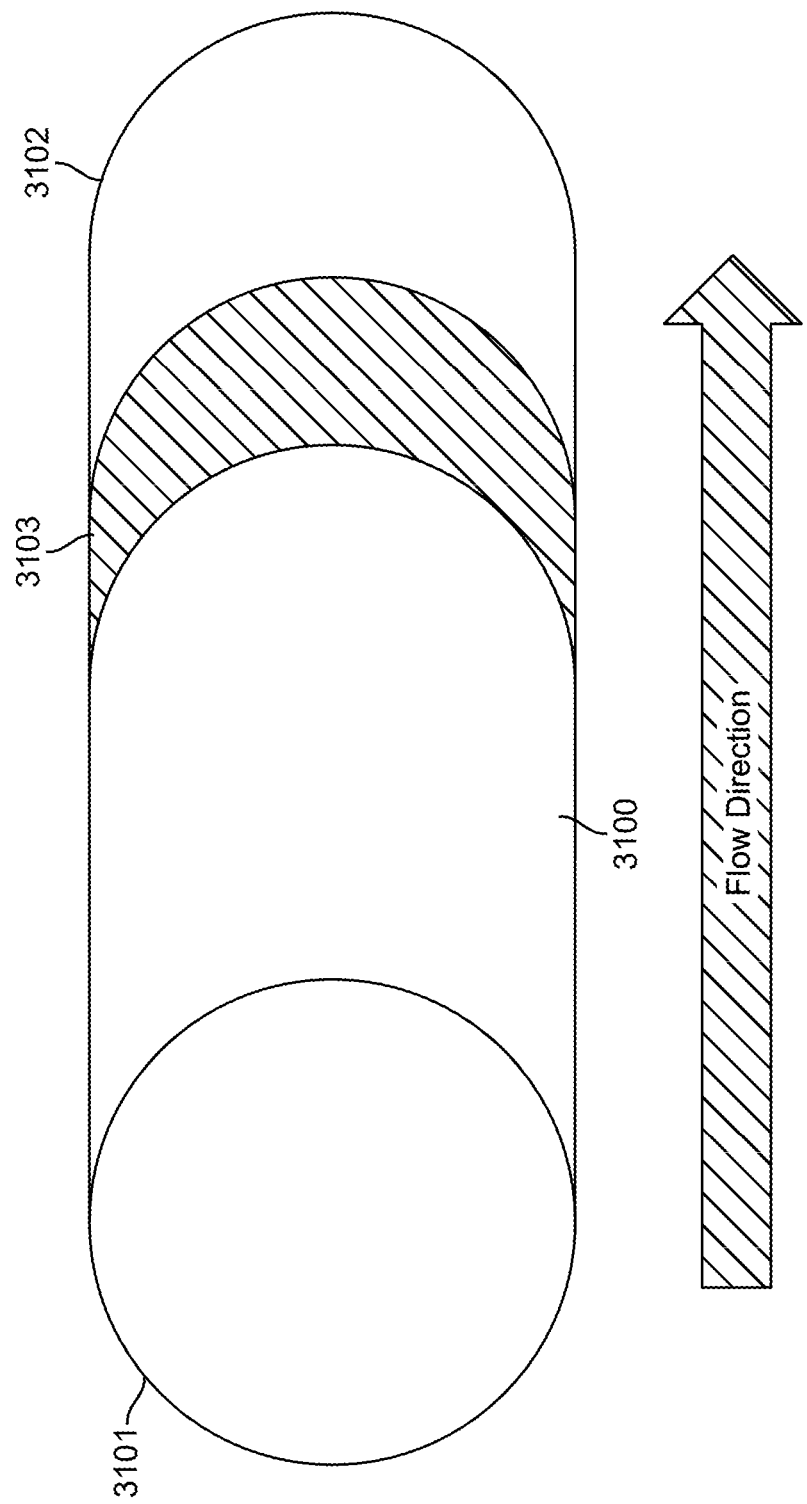
FIGS. 31-33 illustrate exemplary sensor positions on a prosthesis.

FIG. 31 is an exemplary embodiment wherein 3100 is a tubular prosthetic having a distal end 3102 and a proximal end 3101 and an acoustic sensor 3103 which is preferably 0-3 cm from 3102 and preferably 0-15 cm from 3101. Element 3103 may form a closed loop around 3100, but can also take on any of the other configurations described herein.

Figure 32:
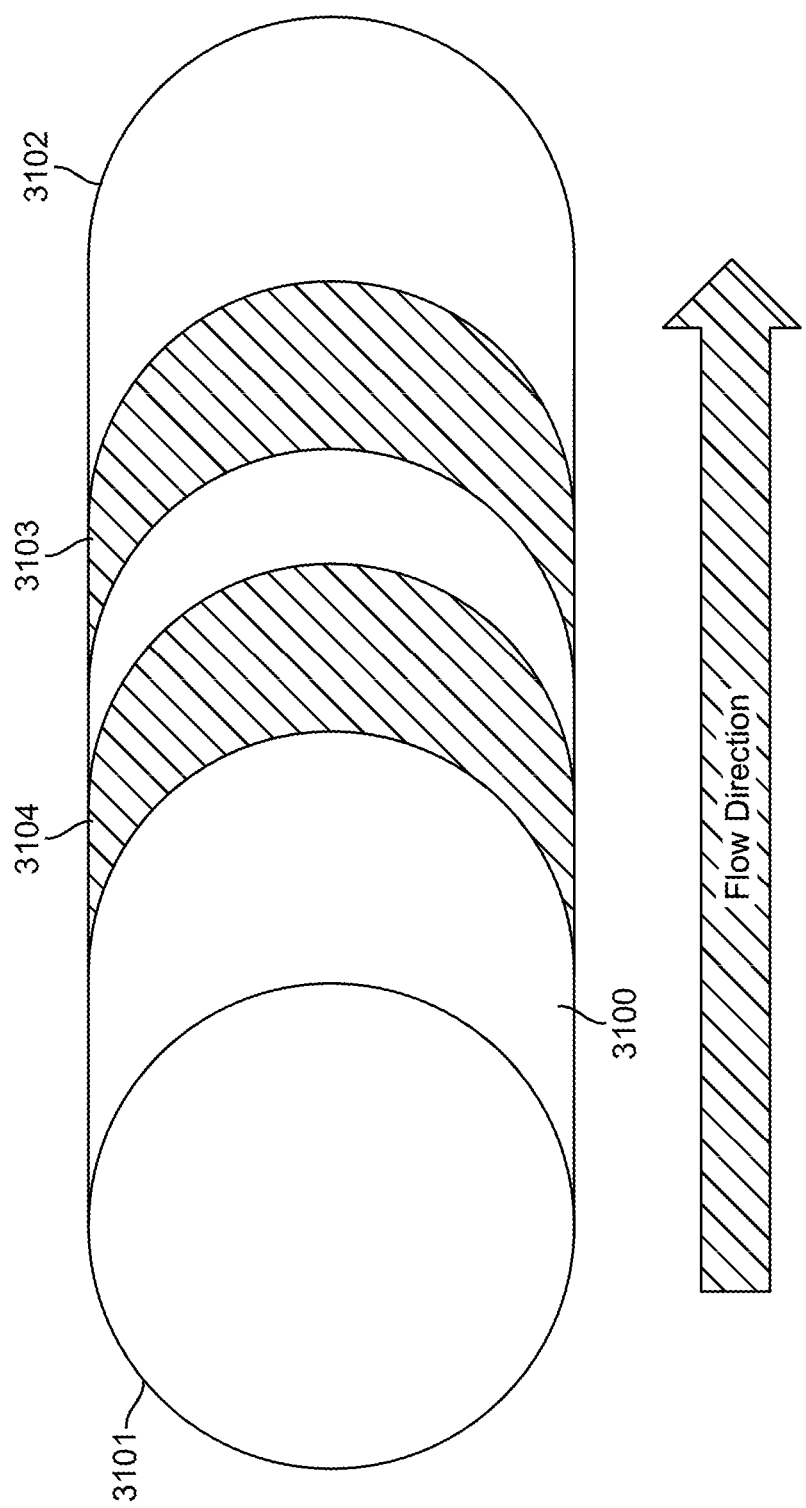

FIG. 32 is another exemplary embodiment wherein 3100 is a tubular prosthetic having a distal end 3102 and a proximal end 3101 and a first acoustic sensor 3103 which is preferably 0-3 cm from 3102, and a second acoustic sensor 3104 which is preferably 0-15 cm from 3101. Element 3103 and element 3104 may each form a closed loop around 3100, but can also take on any of the other configurations described herein.

Figure 33:
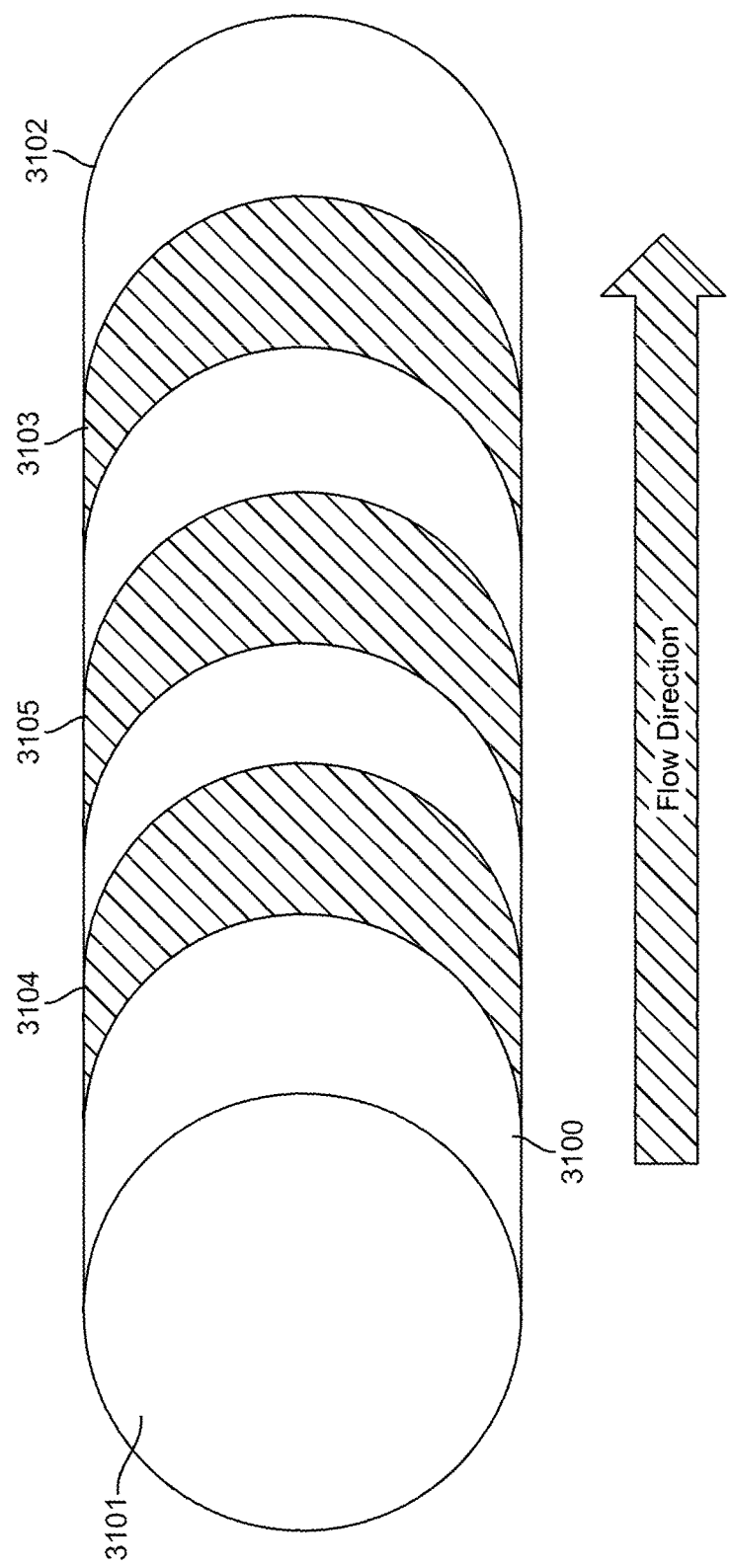

FIG. 33 is another exemplary embodiment wherein element 3100 is a tubular prosthetic having a distal end 3102 and a proximal end 3101 and a first acoustic sensor 3103 which is preferably 0-3 cm from element 3102, a second acoustic sensor 3104 which is preferably 0-15 cm from element 3101, and a third acoustic sensor which is preferably 0-18 cm proximal to element 3103 and preferably 0-18 cm distal to element 3104. Elements 3103, 3104 and 3105 may each form a closed loop around 3100, but can also take on any of the other configurations described herein.

It is therefore now possible to provide in any of the exemplary embodiments described herein, a sensor that may be coupled to a prosthesis that can detect an occlusion such as a stenotic region either proximal to or distal of the sensor. The sensor is preferably implanted into the patient or animal and can provide a signal to an external device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A prosthesis for monitoring a stenosis therein, said prosthesis comprising:
   a tubular prosthesis having a proximal portion, a distal portion, and a lumen extending therebetween; and
   a sensor coupled to the tubular prosthesis and disposed at an effective predetermined location on the tubular prosthesis,
   wherein the sensor is disposed circumferentially around the tubular prosthesis, and forms a loop around the tubular prosthesis; and
   wherein the sensor is configured to sense a presence of the stenosis in the lumen.

2. The prosthesis of claim 1, wherein the sensor comprises an acoustic sensor.

3. The prosthesis of claim 1, wherein the sensor is disposed in the proximal portion or the distal portion.

4. The prosthesis of claim 1, wherein the stenosis is disposed distal of the sensor, and wherein the sensor is configured to sense the presence of the stenosis in the lumen.

5. The prosthesis of claim 1, wherein the sensor is disposed no more than 0 cm to about 3 cm away from the stenosis.

6. The prosthesis of claim 1, wherein the tubular prosthesis is a graft and the proximal portion of the prosthesis is adapted to be coupled to a native fluid conduit at a proximal anastomotic site, and wherein the distal portion of the prosthesis is adapted to be coupled to the native fluid conduit at a distal anastomotic site, and wherein the sensor is disposed no more than 0 cm to about 3 cm away from the distal anastomotic site.

7. The prosthesis of claim 1, wherein the tubular prosthesis is a graft and the proximal portion of the prosthesis is adapted to be coupled to a native fluid conduit at a proximal anastomotic site, and wherein the distal portion of the prosthesis is adapted to be coupled to the native fluid conduit at a distal anastomotic site, and wherein the sensor is disposed no more than 0 cm to about 15 cm away from the proximal anastomotic site.

8. The prosthesis of claim 6, wherein the native fluid conduit comprises a blood vessel.

9. The prosthesis of claim 7, wherein the native fluid conduit comprises a blood vessel.

10. The prosthesis of claim 1, wherein the tubular prosthesis is a stent or a stent-graft.

11. The prosthesis of claim 1, wherein only a single sensor is coupled to the prosthesis.

12. The prosthesis of claim 1, wherein the prosthesis comprises a plurality of sensors disposed on the tubular prosthesis and spaced a predetermined distance apart from one another, thereby allowing the plurality of sensors to detect the stenosis, wherein the stenosis forms along any portion of the tubular prosthesis.

13. The prosthesis of claim 1, wherein the prosthesis is a stent, and wherein the prosthesis further comprises a plurality of sensors disposed on the stent and spaced a predetermined distance apart from one another, thereby allowing the plurality of sensors to detect the stenosis, wherein the stenosis forms along any portion of the stent.

14. The prosthesis of claim 12, wherein the predetermined distance is about 18 cm.

15. The prosthesis of claim 13, wherein the predetermined distance is about 18 cm.

16. A method for monitoring a stenosis in a prosthesis, said method comprising:
    providing a tubular prosthesis having a sensor coupled thereto;
    implanting the tubular prosthesis in a native fluid conduit;
    sensing a stenosis in a lumen of the tubular prosthesis with the sensor; and
    reporting out data from the sensor regarding a condition of the stenosis;
    wherein sensing comprises circumferentially sensing the stenosis with the sensor, wherein the sensor is circumferentially disposed around the tubular prosthesis.

17. The method of claim 16, wherein the sensor is an acoustic sensor, and wherein sensing the stenosis comprises acoustically sensing the stenosis with the acoustic sensor.

18. The method of claim 16, wherein sensing comprises sensing the stenosis with the sensor disposed in a proximal portion or a distal portion of the tubular prosthesis.

19. The method of claim 16, wherein sensing comprises sensing the stenosis with the sensor disposed no more than 0 cm to about 3 cm away from the stenosis.

20. The method of claim 16, wherein the tubular prosthesis is a graft, and wherein implanting the tubular prosthesis comprises forming a distal anastomosis between the native fluid conduit and a distal portion of the graft, and wherein the sensing comprises sensing the stenosis with the sensor disposed no more than 0 cm to about 3 cm away from the distal anastomosis.

21. The method of claim 16, wherein the tubular prosthesis is a graft, and wherein implanting the tubular prosthesis comprising forming a proximal anastomosis between the native fluid conduit and a proximal portion of the graft, and wherein the sensing comprises sensing the stenosis with the sensor disposed no more than 0 cm to about 15 cm away from the proximal anastomosis.

22. The method of claim 16, wherein sensing comprises sensing the stenosis with the sensor when the stenosis is distal of the sensor.

23. The method of claim 16, wherein the native fluid conduit comprises a blood vessel.

24. The method of claim 16, wherein the sensing comprises sensing the stenosis with only a single sensor coupled to the prosthesis.

25. The method of claim 16, wherein the sensor comprises a plurality of sensors disposed on the tubular prosthesis and spaced a predetermined distance apart from one another, and wherein sensing the stenosis comprises sensing the stenosis from any position along a length of the tubular prosthesis.

26. The method of claim 25, wherein the predetermined distance is approximately 18 cm.

27. The method of claim 16, wherein the tubular prosthesis is a stent, a graft, or a stent-graft.

* * * * *